US009557321B2

(12) United States Patent
Nakahata et al.

(10) Patent No.: US 9,557,321 B2
(45) Date of Patent: Jan. 31, 2017

(54) METHOD FOR SCREENING DRUGS FOR SUPPRESSING INFLAMMASOME ACTIVITY

(75) Inventors: Tatsutoshi Nakahata, Kyoto (JP); Megumu Saito, Kyoto (JP); Takayuki Tanaka, Kyoto (JP); Shinya Yamanaka, Kyoto (JP)

(73) Assignee: KYOTO UNIVERSITY, Kyoto-shi, Kyoto (JP)

( * ) Notice: Subject to any disclaimer, the term of this patent is extended or adjusted under 35 U.S.C. 154(b) by 353 days.

(21) Appl. No.: 13/885,950

(22) PCT Filed: Nov. 17, 2011

(86) PCT No.: PCT/JP2011/077265
§ 371 (c)(1),
(2), (4) Date: May 16, 2013

(87) PCT Pub. No.: WO2012/067265
PCT Pub. Date: May 24, 2012

(65) Prior Publication Data
US 2013/0273588 A1   Oct. 17, 2013

Related U.S. Application Data

(60) Provisional application No. 61/415,102, filed on Nov. 18, 2010.

(51) Int. Cl.
| | |
|---|---|
| *C12N 5/00* | (2006.01) |
| *G01N 33/50* | (2006.01) |
| *C12N 5/074* | (2010.01) |
| *G01N 33/68* | (2006.01) |

(52) U.S. Cl.
CPC ......... *G01N 33/5055* (2013.01); *C12N 5/0696* (2013.01); *G01N 33/6869* (2013.01); *G01N 33/6872* (2013.01); *G01N 2333/545* (2013.01); *G01N 2500/10* (2013.01)

(58) Field of Classification Search
CPC ............ G01N 33/5055; G01N 33/6872; C12N 5/0696
See application file for complete search history.

(56) References Cited

U.S. PATENT DOCUMENTS

2008/0008652 A1*   1/2008   Nunez et al. ............ 424/9.2

FOREIGN PATENT DOCUMENTS

| WO | WO 2010/042669 A2 | 4/2010 |
| WO | WO 2011/074690 A1 | 6/2011 |

OTHER PUBLICATIONS

Saito et al. Arthritis and Rheumatism 52(11):3579-3585, 2005.*
OMIM entry printout from www.omim.org/entry/606416. Printed Jul. 31, 2015. pp. 1-11.*
Inflammasome printout from en.Wikipedia.org/wiki/Inflammasome. pp. 1-4, printed Jul. 31, 2015.*
Dostert C. et al., Innate Immune Activation Through Nalp3 Inflammasome Sensing of Asbestos and Silica, Science, vol. 320, pp. 674-677, 2008.
Halle A. et al, The NALP3 inflammasome is involved in the innate immune response to amyloid-$\beta$, Nature Immunology, vol. 9, pp. 857-865, 2008.
Kambe N. et al., IL-1$\beta$ Secretion Through Inflammasome and Histamine-independent Urticariam J Environ Dermatol Cutan Allergol, vol. 4, No. 4, pp. 185-191, 2010.
Kambe N. et al., The Inflammasome, an Innate Immunity Guardian, Participates in Skin Urticarial Reactions and Contact Hypersensitivity, Allergology International, vol. 59, No. 2, pp. 105-113, 2010.
Kubota T. et al., Cryopyrin-associated periodic syndromes: background and therapeutics, Mod Rheumatol, vol. 20, No. 3, pp. 213-221, 2010.
Martinon F. et al., Gout-associated uric acid crystals activate the NALP3 inflammasome, Nature, vol. 440, pp. 237-241, 2006.
Masters S.L. et al., Activation on the NLRP3 inflammasome by islet amyloid polypeptide provides a mechanism for enhanced IL-1$\beta$ in type 2 diabetes, Nature Immunology, vol. 11, pp. 897-904, 2010.
Meng G. et al., A Mutation in the Nlrp3 Gene Causing Inflammasome Hyperactivation Potentiates Th17 Cell-Dominant Immune Responses, Immunity, vol. 30, No. 6, pp. 860-874, 2009.
Meng G. et al., New insights into the nature of autoinflammatory diseases from mice with Nlrp3 mutations, Eur. J. Immunol., vol. 40, No. 3, pp. 649-653, 2010.
Peter D. et al., NLRP3 inflamasomes are requires for the atherogenesis and activated by cholesterol crystals that form early in disease, Nature, vol. 464, pp. 1357-1361, 2010.
Senju S. et al., Characterization of Dendritic Cells and Macrophages Generated by Directed Differentiation from Mouse Induced Pluripotent Stem Cells, Stem Cellls, vol. 27, No. 5, pp. 1021-1031, 2009.
International Search Report re Application No. PCT/JP2011/077265 mailed on Jan. 24, 2012.
Dowds et al., "Cryopyrin-induced Interleukin 1$\beta$ Secretion in Monocytic Cells," *The Journal of Biological Chemistry*, vol. 279(21), pp. 21924-21928 (2004).
Juliana et al., "Anti-inflammatory Compounds Parthenolide and Bay 11-7082 are Direct Inhibitors of the Inflammasome," *The Journal of Biological Chemistry*, vol. 285(13), pp. 9792-9802 (Mar. 26, 2010).
Saito et al., "Disease Modeling of a NLRP3-drived Autoinflammatory Disease with Induced Pluripotent Stem Cells," *Inflamm. Res.*, vol. 60(1), Suppl. 1, p. S288 (2011).
Extended European Search Report for European Patent Application No. 11842110.6, dated Apr. 11, 2014.

* cited by examiner

*Primary Examiner* — Marcia S Noble
(74) *Attorney, Agent, or Firm* — Knobbe, Martens, Olson & Bear LLP

(57)   ABSTRACT

The present invention provides a method for screening drugs for suppressing inflammasome activity, using macrophages derived from induced pluripotent stem cells (iPS cells) having mutant NLRP3 gene.

12 Claims, 5 Drawing Sheets

Wild type

Mutant type

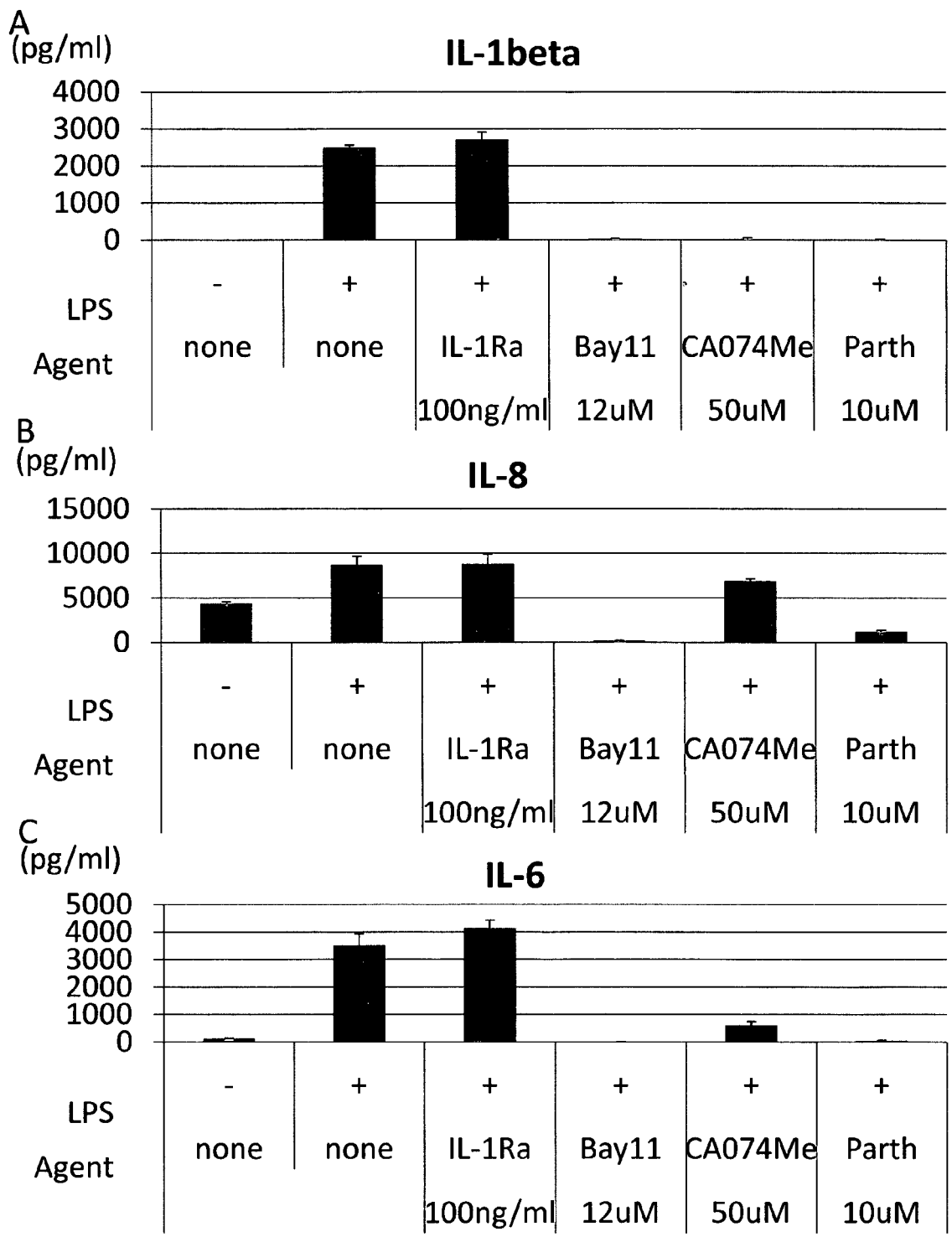

METHOD FOR SCREENING DRUGS FOR SUPPRESSING INFLAMMASOME ACTIVITY

CROSS-REFERENCE TO RELATED APPLICATIONS

This application is the U.S. National Phase under 35 U.S.C. §371 of International Application PCT/JP2011/077265, filed Nov. 17, 2011, which claims priority to U.S. Provisional Application No. 61/415,102, filed Nov. 18, 2010.

Reference to Sequence Listing

This application incorporates by reference the sequence listing submitted as ASCII text filed via EFS-Web on Feb. 10, 2016. The Sequence Listing is provided as a file entitled "20160208 SEQ LST REV TOYA166007APC.txt," created on Feb. 8, 2016, and which is approximately 73 kilobytes in size.

TECHNICAL FIELD

The present invention relates to a method for screening drugs for suppressing inflammasome activity.

BACKGROUND ART

The innate immune response, in which a signal such as amyloid β, asbestos, urate crystals, cholesterol crystals, or oligomers of islet amyloid polypeptides triggers formation of complexes called inflammasomes containing NLRP3, an adaptor protein ASC and caspase-1, followed by activation of caspase-1, leading to production of IL-1β, is considered to be one of the causes of Alzheimer's disease, asbestosis, gout, arteriosclerosis, type 2 diabetes and the like (Halle A, et al., Nat Immunol. 9:857-65, 2008; Dostert C, et al., Science vol. 320, pp. 674-677, 2008; Peter D, et al., Nature 464: 1357-1361, 2010; Martinon F, et al., Nature 440:237-41, 2006; Masters SL, et al., Nat Immunol. 11:897-904, 2010).

On the other hand, CINCA (Chronic Infantile Neurologic Cutaneous and Articular) syndrome is one of autoinflammatory syndromes and about a half of patients suffering from this syndrome have a heterozygous mutation in the NLRP3 gene. This mutant NLRP3 gene is said to cause systemic inflammation by constantly activating the above-described inflammasomes.

However, a screening system suitable for developing drugs for suppressing an activity of inflammasome containing NLRP3, which is common among these diseases, has not yet been developed.

DISCLOSURE OF THE INVENTION

The present invention aims to provide a screening method for development of drugs for suppressing inflammasome activity.

The inventors of the present invention introduced reprogramming factors into somatic cells of a patient suffering from CINCA syndrome and thereby prepared induced pluripotent stem cells (iPS cells) having mutant NLRP3 gene and iPS cells having wild-type NLRP3 gene from the same patient. These iPS cells were induced to differentiate into macrophages and the resulting macrophages were subjected to LPS stimulation. As a result, macrophages derived from iPS cells having mutant NLRP3 gene were confirmed to produce a much larger amount of IL-1β than macrophages derived from iPS cells having wild-type NLRP3 gene, and it was found that this phenomenon can be used as an index for screening drugs for diseases caused by inflammasomes.

The inventors of the present invention also carried out differentiation induction into macrophages and the resulting macrophages were subjected to LPS stimulation. As a result, macrophages derived from iPS cells having mutant NLRP3 gene were found to show aggregation of ASC in the cells, and it was found that this phenomenon can be used as an index for screening drugs for diseases caused by inflammasomes.

The present invention was completed based on these findings.

It is an aspect of the present invention to provide a method for screening a drug for suppressing inflammasome activity, comprising the steps of:

(1) contacting a test substance with LPS-stimulated macrophages derived from iPS cells having mutant NLRP3 gene;

(2) measuring the amount of IL-1β secretion from the macrophages after step (1); and (3) selecting the test substance as a drug for suppressing inflammasome activity when the amount of IL-1β secretion measured in step (2) is smaller than the amount of IL-1β secretion from macrophages derived from iPS cells having mutant NLRP3 gene which are stimulated with LPS but not contacted with the test substance.

It is another aspect of the present invention to provide a method for screening a drug for suppressing inflammasome activity, comprising the steps of:

(1) contacting a test substance with LPS-stimulated macrophages derived from iPS cells having mutant NLRP3 gene;

(2) measuring the amount of IL-1β secretion from the macrophages after step (1); and (3) selecting the test substance as a drug for suppressing inflammasome activity when the amount of secretion measured in step (2) is equivalent to or less than the amount of IL-1β secretion from LPS-stimulated macrophages derived from iPS cells having wild-type NLRP3 gene.

It is another aspect of the present invention to provide a method for screening a drug for suppressing inflammasome activity, comprising the steps of:

(1) contacting a test substance with LPS-stimulated macrophages derived from iPS cells having mutant NLRP3 gene and with LPS-stimulated macrophages derived from iPS cells having wild-type NLRP3 gene;

(2) measuring the amount of IL-1β secretion from the respective macrophages after step (1); and (3) selecting the test substance as a drug for suppressing inflammasome activity when the amount of IL-1β secretion from the macrophages derived from iPS cells having mutant NLRP3 gene measured in step (2) is smaller than the amount of IL-1β secretion from macrophages derived from iPS cells having mutant NLRP3 gene which are stimulated with LPS but not contacted with the test substance, and the amount of IL-1β secretion from the macrophages derived from iPS cells having wild-type NLRP3 gene measured in step (2) is equivalent to the amount of IL-1β secretion from macrophages derived from iPS cells having wild-type NLRP3 gene which are stimulated with LPS but not contacted with the test substance.

It is an aspect of the present invention to provide the method as described above, wherein said drug for suppressing inflammasome activity is a therapeutic agent for asbestosis, Alzheimer's disease, type 2 diabetes, atherosclerotic cardiovascular disease, gout, or cryopyrin-associated periodic syndrome.

It is another aspect of the present invention to provide the method as described above, wherein said mutant NLRP3 gene is NLRP3 gene in which adenine at position 1709 is mutated to guanine.

It is another aspect of the present invention to provide the method as described above, wherein macrophages derived from iPS cells having wild-type NLRP3 gene are further stimulated with ATP.

It is another aspect of the present invention to provide the method as described above, wherein said iPS cells having mutant NLRP3 gene and said iPS cells having wild-type NLRP3 gene are iPS cells derived from the same individual.

It is another aspect of the present invention to provide a method for screening a drug for suppressing inflammasome activity, comprising the steps of:

(1) contacting a test substance with LPS-stimulated macrophages derived from iPS cells having mutant NLRP3 gene;

(2) measuring the ratio of macrophages having aggregated ASC after step (1); and (3) selecting the test substance as a drug for suppressing inflammasome activity when the ratio measured in step (2) is smaller than the ratio of macrophages having aggregated ASC in macrophages derived from iPS cells having mutant NLRP3 gene which are stimulated with LPS but not contacted with the test substance.

It is another aspect of the present invention to provide a method for screening a drug for suppressing inflammasome activity, comprising the steps of:

(1) contacting a test substance with LPS-stimulated macrophages derived from iPS cells having mutant NLRP3 gene;

(2) measuring the ratio of macrophages having aggregated ASC after step (1); and (3) selecting the test substance as a drug for suppressing inflammasome activity when the ratio measured in step (2) is equivalent to or less than the ratio of macrophages having aggregated ASC in LPS-stimulated macrophages derived from iPS cells having wild-type NLRP3 gene.

It is another aspect of the present invention to provide a method for screening a drug for suppressing inflammasome activity, comprising the steps of:

(1) contacting a test substance with LPS-stimulated macrophages derived from iPS cells having mutant NLRP3 gene and with LPS-stimulated macrophages derived from iPS cells having wild-type NLRP3 gene;

(2) measuring the ratio of macrophages having aggregated ASC in the respective macrophages after step (1); and (3) selecting the test substance as a drug for suppressing inflammasome activity when the ratio of macrophages having aggregated ASC in the macrophages derived from iPS cells having mutant NLRP3 gene measured in step (2) is smaller than the ratio of macrophages having aggregated ASC in macrophages derived from iPS cells having mutant NLRP3 gene which are stimulated with LPS but not contacted with the test substance, and the ratio of macrophages having aggregated ASC in the macrophages derived from iPS cells having wild-type NLRP3 gene measured in step (2) is equivalent to the ratio of macrophages having aggregated ASC in macrophages derived from iPS cells having wild-type NLRP3 gene which are stimulated with LPS but not contacted with the test substance.

It is another aspect of the present invention to provide the method as described above, wherein said drug for suppressing inflammasome activity is a therapeutic agent for asbestosis, Alzheimer's disease, type 2 diabetes, atherosclerotic cardiovascular disease, gout, or cryopyrin-associated periodic syndrome.

It is another aspect of the present invention to provide the method as described above, wherein said mutant NLRP3 gene is NLRP3 gene in which adenine at position 1709 is mutated to guanine.

It is another aspect of the present invention to provide the method as described above, wherein macrophages derived from iPS cells having wild-type NLRP3 gene are further stimulated with ATP.

It is another aspect of the present invention to provide the method as described above, wherein said iPS cells having mutant NLRP3 gene and said iPS cells having wild-type NLRP3 gene are iPS cells derived from the same individual.

It is another aspect of the present invention to provide a kit for screening a drug for suppressing inflammasome activity, comprising macrophages derived from iPS cells having mutant NLRP3 gene.

BRIEF DESCRIPTION OF THE DRAWINGS

FIG. 5 shows the amount of secretion of IL-1β (A), IL-8 (B) and IL-6 (C), in macrophages derived from iPS cells in the cases of (1) no LPS stimulation and no drug addition, (2) LPS stimulation and no drug addition, (3) LPS stimulation and Interleukin 1 receptor antagonist (IL-1Ra) addition, (4) LPS stimulation and Bay11-7028 (Bay11) addition, (5) LPS stimulation and CA074Me addition, and (6) LPS stimulation and Parthenolide (Parth) addition.

DESCRIPTION OF THE EMBODIMENTS

Figure 1:
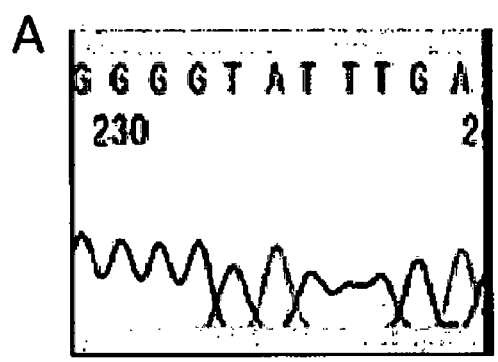
FIG. 1 shows results of sequencing of a part of Exon 3 of NLRP3 gene in (A) wild-type and (B) mutant. It was shown that the nucleotide at position 1709 of NLRP3 is A/G in the mutant.
Figure 1:
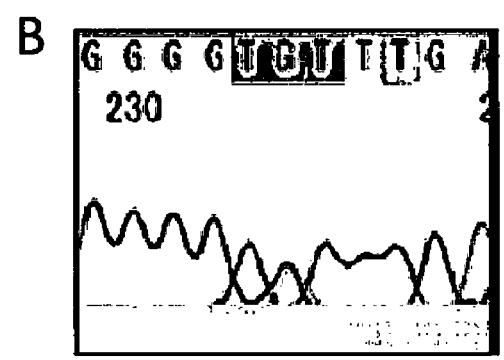

The present invention provides a method for screening drugs for suppressing inflammasome activity using macrophages obtained by differentiation induction of induced pluripotent stem cells (iPS cells) having mutant NLRP3 gene and/or iPS cells having wild-type NLRP3 gene. In the present specification, NLRP3 means NLR family, pyrin domain containing 3, which is known to have 5 types of variants, and the NLRP3 may be any of these variants. In the present invention, examples of the NLRP3 include NCBI accession numbers $NM_{13}$ 004895 (SEQ ID NO: 1), $NM_{13}$ 183395 (SEQ ID NO: 2), $NM_{13}$ 001079821 (SEQ ID NO: 3), NM_001127461(SEQ ID NO: 4) and NM$_{13}$ 001127462 (SEQ ID NO: 5). Here, the translation initiation codon in the NLRP3 is preferably the codon located 6 nucleotides downstream of the translation initiation codon described in each of these NCBI accession numbers. Examples of the mutant NLRP3 gene include NLRP3 gene wherein adenine at position 1709 counted from the translation initiation codon (in the case of the coding region shown in the NCBI accession numbers, position 1715 counted from the translation initiation codon) is guanine, cytosine at position 1043 (position 1049 in the coding region shown in the NCBI accession numbers) counted from the translation initiation codon is thymine, or guanine at position 587 (position 593 in the coding region shown in the NCBI accession numbers) counted from the translation initiation codon is adenine. The NLRP3 is preferably the one wherein the nucleotide at position 1709 is mutated to guanine.

Method for Producing iPS Cells

The iPS cells used in the present invention can be prepared by introducing certain specific nuclear reprogramming substances into somatic cells in the form of DNA or protein, or by increasing expression of endogenous mRNAs and proteins of the nuclear reprogramming substances by an agent(s) (K. Takahashi and S. Yamanaka (2006) Cell, 126: 663-676; K. Takahashi et al. (2007) Cell, 131:861-872; J. Yu et al. (2007) Science, 318:1917-1920; M. Nakagawa et al. (2008) Nat. Biotechnol., 26:101-106; WO 2007/069666; and WO 2010/068955). The nuclear reprogramming substances are not restricted as long as these are genes specifically expressed in ES cells, or genes playing important roles in maintenance of the undifferentiated state of ES cells, or gene products thereof, and examples thereof include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb and Esrrg. These reprogramming substances may be used in combination when iPS cells are to be established. For example, the combination may contain at least one, two or three of the above reprogramming substances, and the combination preferably contains four of the above reprogramming substances.

The information on the nucleotide sequences of mouse and human cDNAs of the above-described respective nuclear reprogramming substances, and the amino acid sequences of the proteins encoded by the cDNAs can be obtained by referring to the NCBI accession numbers described in WO 2007/069666. Further, the information on the mouse and human cDNA sequences and amino acid sequences of each of L-Myc, Lin28, Lin28b, Esrrb and Esrrg can be obtained by referring to the NCBI accession numbers described below. Those skilled in the art can prepare desired nuclear reprogramming substances by a conventional method based on the information on the cDNA sequences or amino acid sequences.

| Gene name | Mouse | Human |
|---|---|---|
| L-Myc | NM_008506 (SEQ ID NO: 8) | NM_001033081 (SEQ ID NO: 9) |
| Lin28 | NM_145833 (SEQ ID NO: 10) | NM_024674 (SEQ ID NO: 11) |
| Lin28b | NM_001031772 (SEQ ID NO: 12) | NM_001004317 (SEQ ID NO: 13) |
| Esrrb | NM_011934 (SEQ ID NO: 14) | NM_004452 (SEQ ID NO: 15) |
| Esrrg | NM_011935 (SEQ ID NO: 16) | NM_001438 (SEQ ID NO: 17) |

These nuclear reprogramming substances may be introduced into somatic cells in the form of protein by a method such as lipofection, binding to a cell membrane-permeable peptide, or microinjection, or in the form of DNA by a method such as use of a vector including a virus, plasmid and artificial chromosome; lipofection; use of liposomes; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (Proc Jpn Acad Ser B Phys Biol Sci. 85, 348-62, 2009). Examples of the artificial chromosome vector include human artificial chromosomes (HACs), yeast artificial chromosomes (YACs) and bacterial artificial chromosomes (BACs, PACs). Examples of the plasmid which may be used include plasmids for mammalian cells (Science, 322:949-953, 2008). The vectors may contain a regulatory sequence(s) such as a promoter, enhancer, ribosome binding sequence, terminator and/or polyadenylation site, to allow expression of the nuclear reprogramming substances. Examples of the promoter to be used include the EF1α promoter, CAG promoter, SRα promoter, SV40 promoter, LTR promoter, CMV (cytomegalovirus) promoter, RSV (Rous sarcoma virus) promoter, MoMuLV (Moloney murine leukemia virus) LTR and HSV-TK (herpes simplex virus thymidine kinase) promoter. Among these, the EF1α promoter, CAG promoter, MoMuLV LTR, CMV promoter, SRα promoter and the like are preferred. The vectors may further contain, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; or the like. Further, in order to remove, after introduction of the above vector into somatic cells, the genes encoding the nuclear reprogramming substances, or both the promoters and the genes encoding the reprogramming substances linked thereto, the vector may have loxP sequences in the upstream and the downstream of these sequences. In another preferred mode, a method may be employed wherein, after incorporation of the transgene(s) into a chromosome(s) using a transposon, transposase is allowed to act on the cells using a plasmid vector or an adenovirus vector, thereby completely removing the transgene(s) from the chromosome(s). Preferred examples of the transposon include piggyBac, which is a transposon derived from a lepidopteran insect (Kaji, K. et al., (2009), Nature, 458: 771-775; Woltjen et al., (2009), Nature, 458: 766-770; and WO 2010/012077). Further, the vector may contain the replication origin of lymphotrophic herpes virus, BK virus or Bovine papillomavirus and sequences involved in their replication, such that the vector can replicate without being incorporated into the chromosome and exist episomally. Examples of such a vector include vectors containing EBNA-1 and oriP sequences and vectors containing Large T and SV40ori sequences (WO 2009/115295; WO 2009/157201; WO 2009/149233). Further, in order to introduce plural nuclear reprogramming substances at the same time, an expression vector which allows polycistronic expression may be used. In order to allow polycistronic expression, the sequences encoding the genes may be linked to each other via IRES or the foot-and-mouth disease virus (FMDV) 2A coding region (Science, 322:949-953, 2008; WO 2009/092042 and WO 2009/152529).

For enhancing the induction efficiency of iPS cells upon the nuclear reprogramming, histone deacetylase (HDAC) inhibitors [for example, low molecular inhibitors such as valproic acid (VPA) (Nat. Biotechnol., 26(7): 795-797 (2008)), trichostatin A, sodium butyrate, MC 1293 and M344; and nucleic acid-type expression inhibitors such as siRNAs and shRNAs against HDAC (e.g., HDAC1 siRNA Smartpool (registered trademark) (Millipore) and HuSH 29mer shRNA Constructs against HDAC1 (OriGene))], DNA methyltransferase inhibitors (e.g., 5'-azacytidine) (Nat. Biotechnol., 26(7): 795-797 (2008)), G9a histone methyltransferase inhibitors [for example, low molecular inhibitors such as BIX-01294 (Cell Stem Cell, 2: 525-528 (2008)); and nucleic acid-type expression inhibitors such as siRNAs and shRNAs against G9a (e.g., G9a siRNA (human) (Santa Cruz Biotechnology))], L-channel calcium agonists (e.g., Bayk8644) (Cell Stem Cell, 3, 568-574 (2008)), p53 inhibitors [e.g., siRNAs and shRNAs against p53 (Cell Stem Cell, 3, 475-479 (2008))], Wnt Signaling activators (e.g., soluble Wnt3a) (Cell Stem Cell, 3, 132-135 (2008)), growth factors such as LIF and bFGF, ALK5 inhibitors (e.g., SB431542) (Nat. Methods, 6: 805-8 (2009)), mitogen-activated protein kinase signaling inhibitors, glycogen synthase kinase-3 inhibitors (PLoS Biology, 6(10), 2237-2247 (2008)), miR-NAs such as miR-291-3p, miR-294 and miR-295 (R L. Judson et al., Nat. Biotech., 27: 459-461 (2009)), and the like may be used in addition to the above-described factors.

Examples of the agent(s) used in the method for increasing expression of the endogenous proteins of nuclear reprogramming substances using an agent include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3 (2H)-benzothiazolyl)ethanone HBr(pifithrin-alpha), prostaglandin J2 and prostaglandin E2 (WO 2010/068955).

Examples of the culture medium for induction of the iPS cells include (1) DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); (2) culture media for ES cells containing bFGF or SCF, for example, culture media for mouse ES cells (e.g., TX-WES medium, Thromb-X) and culture media for primate ES cells (e.g., culture medium for primate (human and monkey) ES cells (ReproCELL Inc., Kyoto, Japan), mTeSR-1).

Examples of the culture method include a method wherein somatic cells and nuclear reprogramming substances (DNAs or proteins) are brought into contact with each other at 37° C. in the presence of 5% $CO_2$ in DMEM or DMEM/F12 medium supplemented with 10% FBS, and the cells are cultured for about 4 to 7 days, followed by replating the cells on feeder cells (e.g., mitomycin C-treated STO cells or SNL cells) and starting culture in a bFGF-containing culture medium for primate ES cells about 10 days after the contact between the somatic cells and the reprogramming substances, thereby allowing ES cell-like colonies to appear about 30 to about 45 days after the contact, or later. To enhance the induction efficiency of iPS cells, the culture may be carried out under a condition wherein the concentration of oxygen is as low as 5 to 10%.

As an alternative culture method, the somatic cells may be cultured on feeder cells (e.g., mitomycin C-treated STO cells or SNL cells) in DMEM medium supplemented with 10% FBS (which may further contain LIF, penicillin/streptomycin, puromycin, L-glutamine, non-essential amino acids, β-mercaptoethanol and/or the like, as appropriate), thereby allowing ES-like colonies to appear after about 25 to about 30 days of the culture, or later.

During the above culture, the culture medium is replaced with a fresh culture medium once every day from Day 2 of the culture. The number of the somatic cells used for nuclear reprogramming is not restricted, and usually within the range of about $5 \times 10^3$ to about $5 \times 10^6$ cells per 100-$cm^2$ area on the culture dish.

In cases where a gene including a drug resistance gene is used as a marker gene, cells expressing the marker gene can be selected by culturing the cells in a culture medium (selection medium) containing the corresponding drug. Cells expressing a marker gene can be detected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

Examples of the "somatic cells" used in the present specification include epithelial cells which are keratinized (e.g., keratinized epidermal cells), mucosal epithelial cells (e.g., epithelial cells of the lingual surface), epithelial cells of exocrine glands (e.g., mammary cells), hormone-secreting cells (e.g., adrenomedullary cells), cells for metabolism and storage (e.g., hepatic cells), luminal epithelial cells constituting boundary surfaces (e.g., type I alveolar cells), luminal epithelial cells in the closed circulatory system (e.g., vascular endothelial cells), ciliated cells having a carrying capacity (e.g., tracheal epithelial cells), extracellular matrix-secreting cells (e.g., fibroblasts), contractile cells (e.g., smooth muscle cells), cells involved in the blood system and the immune system (e.g., T lymphocytes), sensory cells (e.g., rod cells), autonomic neurons (e.g., cholinergic neurons), supporting cells of sense organs and peripheral neurons (e.g., satellite cells), nerve cells and glial cells in the central nervous system (e.g., astroglial cells) and pigment cells (e.g., retinal pigment epithelial cells), and progenitor cells (tissue progenitor cells) thereof. The level of differentiation of the somatic cells is not restricted, and either undifferentiated progenitor cells (including somatic stem cells) or terminally-differentiated mature cells may be similarly used as the source of the somatic cells in the present invention. Here, examples of the undifferentiated progenitor cells include tissue stem cells (somatic stem cells) such as neural stem cells, hematopoietic stem cells, mesenchymal stem cells and dental pulp stem cells.

In the present invention, somatic cells having a mutation of NLRP3 and somatic cells having no such a mutation of NLRP3 are preferably obtained from the same individual. The iPS cells are preferably established from a patient suffering from CINCA (Chronic Infantile Neurologic Cutaneous and Articular).

The mutant NLRP3 gene may be one which has been originally retained by the somatic cells from which the iPS cells are derived; or the mutation may be introduced to NLRP3 gene using homologous recombination after establishment of the iPS cells. The homologous recombination may be carried out using a method well known to those skilled in the art.

Method of Differentiation Induction into Macrophages

For producing macrophages from the thus obtained iPS cells, a differentiation induction method comprising the following steps may be used:

(1) culturing iPS cells on OP9 cells;
(2) separating cells using an angioblast marker as an index;
(3) culturing the separated cells on OP9 cells; and
(4) separating/purifying cells using a macrophage marker as an index.

The macrophages in the present invention are cells expressing any or all of CD11b, CD14 and CD68, preferably cells expressing CD 14. Examples of the angioblast marker include CD34, KDR and TRA-1-85.

Prior to Step (1), the iPS cells may be dissociated by an arbitrary method. The dissociation may be carried out either mechanically or by using a dissociation solution having a protease activity and a collagenase activity (e.g., Accutase™, Accumax™ or a cell detachment liquid for primate ES cells (ReproCELL Inc.)) or a separation liquid having only a collagenase activity.

Examples of the coating agent employed in Step (1) and Step (3) include Matrigel (BD), type I collagen, type IV collagen, gelatin, laminin, heparan sulfate proteoglycan and entactin, and combinations thereof.

The culture medium for producing macrophages can be prepared by using, as a basal medium, a culture medium used for culturing animal cells. Examples of the basal medium include IMDM medium, Medium 199 medium, Eagle's Minimum Essential Medium (EMEM), αMEM medium, Dulbecco's modified Eagle's Medium (DMEM), Ham's F12 medium, RPMI 1640 medium and Fischer's medium, and mixed media thereof. The culture medium is preferably αMEM medium. Further, the culture medium may be either a serum-containing medium or a serum-free medium. As required, the culture medium may contain one or more of serum replacements such as albumin, transferrin, Knockout Serum Replacement (KSR) (a serum replacement of FBS for culturing ES cells), fatty acid, insulin, collagen precursor, minor element, 2-mercaptoethanol and 3'-thiolglycerol; and/or may contain one or more of lipids, amino acids, L-glutamine, Glutamax (Invitrogen), non-essential amino acids, vitamins, antibiotics, antioxidants, pyruvic acid, buffers, inorganic salts, N2 supplement (Invitrogen), B27 supplement (Invitrogen), cytokines such as VEGF, stem cell factor (SCF), IL-3, thrombopoietin (TPO), FLT-3 ligand (FL) and macrophage colony-stimulating factor (M-CSF), and the like. Examples of a preferred medium include αMEM containing 10% FCS and VEGF in Step (1), and αMEM containing 10% FCS, SCF, IL-3, TPO, FL and M-CSF in Step (3).

The culture temperature is not restricted and may be about 30 to 40° C., preferably about 37° C., and the culture is carried out under atmosphere of $CO_2$-containing air, wherein the $CO_2$ concentration is preferably about 2 to 5%. The culturing time is not restricted, and, for example, 5 days to 15 days, more preferably 10 days in Step (1); and, for example, 10 days to 20 days, more preferably 16 days in Step (3).

Angioblast marker-positive cells or macrophage marker-positive cells can be separated/purified from cells stained with an antibody for each marker using a flow cytometer or magnetic beads having the antibody by a method well known to those skilled in the art.

Screening Method

The present invention provides a method for screening a drug for suppressing inflammasome activity. The inflammasomes means complexes composed of NLRP3, ASC and caspase-1. The activation of inflammasomes is not restricted, and, for example, it means activation of caspase-1 via formation of the above complexes.

The drug for suppressing inflammasome activity can be used as a therapeutic agent or prophylactic agent for diseases caused by activation of inflammasomes, and examples of the diseases caused by activation of inflammasomes include, but are not limited to, asbestosis, Alzheimer's disease, type 2 diabetes, atherosclerotic cardiovascular disease, gout and cryopyrin-associated periodic syndrome.

Inflammasome activity does not increase upon LPS stimulation in macrophages derived from iPS cells having wild-type NLRP3 gene whereas inflammasome activity increases upon LPS stimulation in macrophages derived from iPS cells having mutant NLRP3 gene.

Thus, in cases where macrophages derived from iPS cells having mutant NLRP3 gene obtained by the above-mentioned method are used, drugs for suppressing inflammasome activity can be screened by:

(1-1) contacting a test substance with LPS-stimulated macrophages derived from iPS cells having mutant NLRP3 gene;

(1-2) measuring the amount of IL-1β secretion from the macrophages after step (1-1); and (1-3) selecting the test substance as a drug for suppressing inflammasome activity when the amount of IL-1β secretion measured in step (1-2) is smaller than the amount of IL-1β secretion from macrophages derived from iPS cells having mutant NLRP3 gene which are stimulated with LPS but not contacted with the test substance.

Here, the LPS stimulation is carried out by adding LPS to the culture of the macrophages. In addition to the LPS stimulation, stimulation with ATP may be carried out. The stimulation time is not restricted and may be, for example, 2 hours to 24 hours in the case of LPS, and 10 minutes to 1 hour in the case of ATP.

In the present invention, the amount of secretion of IL-1β can be measured using the culture supernatant of the macrophages, and examples of the measurement method include immunoassays. Examples of the immunoassays include the radioimmunoassay, enzyme immunoassay, fluoroimmunoassay, luminescence immunoassay, immunoprecipitation, turbidimetric immunoassay, Western blotting and immunodiffusion, and the immunoassay is preferably the enzyme immunoassay, especially preferably the enzyme-linked immunosorbent assay (ELISA) (e.g., sandwich ELISA).

Another example of the method for screening drugs for suppressing inflammasome activity includes a method comprising the steps of:

(2-1) contacting a test substance with LPS-stimulated macrophages derived from iPS cells having mutant NLRP3 gene;

(2-2) measuring the ratio of macrophages having aggregated ASC after step (2-1); and (2-3) selecting the test substance as a drug for suppressing inflammasome activity when the ratio measured in step (2-2) is smaller than the ratio of macrophages having aggregated ASC in macrophages derived from iPS cells having mutant NLRP3 gene which are stimulated with LPS but not contacted with the test substance.

In the present invention, ASC is the apoptosis-associated speck-like protein containing a CARD, which is a protein also referred to as PYCARD. Examples of variants of the gene encoding ASC include, but are not limited to, NCBI accession numbers $NM_{13}$ 013258 (SEQ ID NO: 6) and NM_145182 (SEQ ID NO:7).

Aggregation of ASC means that ASC is not widely distributed in the cell and is localized to form clusters. Aggregation of ASC occurs when macrophages are stimulated with LPS, and can be preferably judged by stronger staining of the areas of localization than the other areas when cells are immunostained using an anti-ASC antibody. An example of preferred aggregation is shown in the left column in FIG. 3B.

The ratio of macrophages having aggregated ASC may be the number of macrophages having aggregated ASC per total macrophages or a certain number of macrophages (e.g., per 10,000 macrophages) or the number of macrophages having aggregated ASC in a culture dish. The aggregation of ASC may be either a single aggregate or a plurality of aggregates in each macrophage.

Other examples of the method for screening drugs for suppressing inflammasome activity include a method comprising the steps of:

(3-1) contacting a test substance with LPS-stimulated macrophages derived from iPS cells having mutant NLRP3 gene;

(3-2) measuring the amount of IL-1β secretion from the macrophages after step (3-1); and (3-3) selecting the test substance as a drug for suppressing inflammasome activity when the amount of secretion measured in step (3-2) is equivalent to or less than the amount of IL-1β secretion from LPS-stimulated macrophages derived from iPS cells having wild-type NLRP3 gene; and a method comprising the steps of (4-1) contacting a test substance with LPS-stimulated macrophages derived from iPS cells having mutant NLRP3 gene;

(4-2) measuring the ratio of macrophages having aggregated ASC after step (4-1); and (4-3) selecting the test substance as a drug for suppressing inflammasome activity when the ratio measured in step (4-2) is equivalent to or less than the ratio of macrophages having aggregated ASC in LPS-stimulated macrophages derived from iPS cells having wild-type NLRP3 gene.

The term "equivalent" includes a case where the value is strictly identical as well as a case where an error preferably within the range of approximately ±5% or more preferably within the range of approximately ±1% exists with respect to the measured value.

In the present invention, the LPS-stimulated macrophages derived from iPS cells having wild-type NLRP3 gene may be further stimulated with ATP before measuring the amount of IL-1β secretion.

Other examples of the method for screening drugs for suppressing inflammasome activity include a method comprising the steps of:

(5-1) contacting a test substance with LPS-stimulated macrophages derived from iPS cells having mutant NLRP3 gene and with LPS-stimulated macrophages derived from iPS cells having wild-type NLRP3 gene;

(5-2) measuring the amount of IL-1β secretion from the respective macrophages after step (5-1); and (5-3) selecting the test substance as a drug for suppressing inflammasome activity when the amount of IL-1β secretion from the macrophages derived from iPS cells having mutant NLRP3 gene measured in step (5-2) is smaller than the amount of IL-1β secretion from macrophages derived from iPS cells having mutant NLRP3 gene which are stimulated with LPS but not contacted with the test substance, and the amount of IL-1β secretion from the macrophages derived from iPS cells having wild-type NLRP3 gene measured in step (5-2) is equivalent to the amount of IL-1β secretion from macrophages derived from iPS cells having wild-type NLRP3 gene which are stimulated with LPS but not contacted with the test substance; and a method comprising the steps of:

(6-1) contacting a test substance with LPS-stimulated macrophages derived from iPS cells having mutant NLRP3 gene and with LPS-stimulated macrophages derived from iPS cells having wild-type NLRP3 gene;

(6-2) measuring the ratio of macrophages having aggregated ASC in the respective macrophages after step (6-1); and (6-3) selecting the test substance as a drug for suppressing inflammasome activity when the ratio of macrophages having aggregated ASC in the macrophages derived from iPS cells having mutant NLRP3 gene measured in step (6-2) is smaller than the ratio of macrophages having aggregated ASC in macrophages derived from iPS cells having mutant NLRP3 gene which are stimulated with LPS but not contacted with the test substance, and the ratio of macrophages having aggregated ASC in the macrophages derived from iPS cells having wild-type NLRP3 gene measured in step (6-2) is equivalent to the ratio of macrophages having aggregated ASC in macrophages derived from iPS cells having wild-type NLRP3 gene which are stimulated with LPS but not contacted with the test substance.

In the screening method of the present invention, an arbitrary test substance can be used, and examples of the test substance include cell extracts, cell culture supernatants, microbial fermentation products, extracts derived from marine organisms, plant extracts, purified proteins and crude proteins, peptides, nonpeptide compounds, synthetic low molecular compounds and naturally occurring compounds. The test compounds can be obtained by using any of a number of approaches in combinatorial library methods known in the art, such as (1) the biological library method, (2) the synthetic library method using deconvolution, (3) the "one-bead one-compound" library method and (4) the synthetic library method using affinity chromatography selection. Application of the biological library method using affinity chromatography selection is limited to peptide libraries, but the other types of approaches can be applied to low-molecular compound libraries of peptides, nonpeptide oligomers or compounds (Lam (1997) Anticancer Drug Des. 12: 145-67). Examples of synthetic methods of molecular libraries are shown in the art (DeWitt et al. (1993) Proc. Natl. Acad. Sci. USA 90: 6909-13; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). The compound libraries may be prepared as solutions (see Houghten (1992) Bio/Techniques 13: 412-21) or beads (Lam (1991) Nature 354: 82-4), chips (Fodor (1993) Nature 364: 555-6), bacteria (U.S. Pat. No. 5,223,409 B), spores (U.S. Pat. No. 5,571,698 B, U.S. Pat. No. 5,403,484 B and U.S. Pat. No. 5,223,409 B), plasmids (Cull et al. (1992) Proc. Natl. Acad. Sci. USA 89: 1865-9) or phages (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US 2002-103360).

Kit for Screening Drugs

The present invention provides a kit for screening drugs for suppressing inflammasome activity. This kit may comprise the above-mentioned cells, reagents and culture medium. The kit may further comprise a document or an instruction that describes a protocol for differentiation induction.

EXAMPLES

Establishment of iPS Cells

Using a retrovirus that expresses human OCT3/4, human SOX2, human KLF4 and human c-MYC as described in Takahashi, K. et al., Cell, 131: 861-872 (2007), 6 clones of iPS cells were established from fibroblasts established from the skin obtained by biopsy from a patient suffering from Chronic Infantile Neurologic, Cutaneous, Articular syndrome (CINCA syndrome) with the patient's consent. Since the patient was a mosaic CINCA syndrome patient, these established iPS cells, irrespective of the fact that these were obtained from the same individual, contained 3 clones having wild-type NLRP3 gene and the other clones having mutant NLRP3 gene in which alanine at position 1709 was mutated to guanine in one of the alleles (FIG. 1).

Method of Differentiation Induction into Macrophages

The iPS cells obtained by the above method were dispersed using CTK solution (Suemori, H et al., Biochem Biophys Res Commun, 35: 926-932 (2006)) and left to stand in a gelatin-coated dish at 37° C. for 60 minutes to remove feeder cells, followed by plating the cells on OP9 cells (Nishikawa, S. I. et al, Development 125, 1747-1757 (1998)). The culture medium used at this time was αMEM containing 10% FCS, antibiotics-antimycotic and 10 ng/ml VEGF. Ten days after the start of the culture, the cells were dispersed using trypsin, and Tra-1-85-positive/CD34-positive/KDR-positive cells were separated and collected using FACS, followed by plating the collected cells on OP9 cells. The culture medium used at this time was αMEM containing 10% FCS, antibiotics-antimycotic, 50 ng/ml hSCF, 50 ng/ml IL-3, 10 ng/ml TPO, 50 ng/ml FL and 50 ng/ml M-CSF. Subsequently, 16 days after the separation and collection of the cells, the cells were suspended using Accumax, and CD 14-positive cells were purified by Magnetic activated cell sorting. The CD 14-positive cells obtained from the 6 clones of iPS cells were used as the macrophages derived from iPS cells, and the 3 macrophages having wild-type NLRP3 gene were designated WT-1, WT-2 and WT-3, respectively, and the 3 macrophages having mutant NLRP3 gene were designated MT-1, MT-2 and MT-3, respectively. Further, control macrophages (201B7) were obtained from 201B7 described in Takahashi, K. et al., Cell, 131: 861-872 (2007) by the same method.

Measurement of Amount of Production of IL-1β

Figure 2:
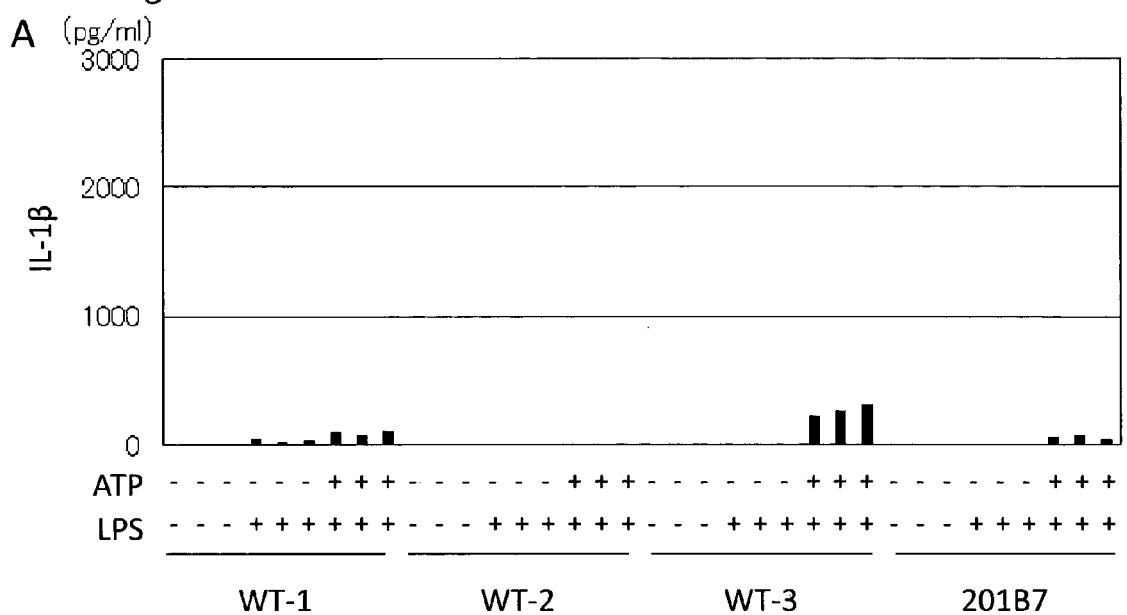
FIG. 2 shows results of measurement of the amount of IL-1β secretion in iPS cells-derived macrophages having (A) wild-type NLRP3 gene and (B) mutant NLRP3 gene, which measurement was carried out for (1) non-addition group, (2) LPS-addition group and (3) LPS- and ATP-addition group. For the wild type, results from 3 clones WT-1, WT-2 and WT-3, and 201B7 (control) are shown. For the mutant type, results from 3 clones MT-1, MT-2 and MT-3 are shown.
Figure 2:
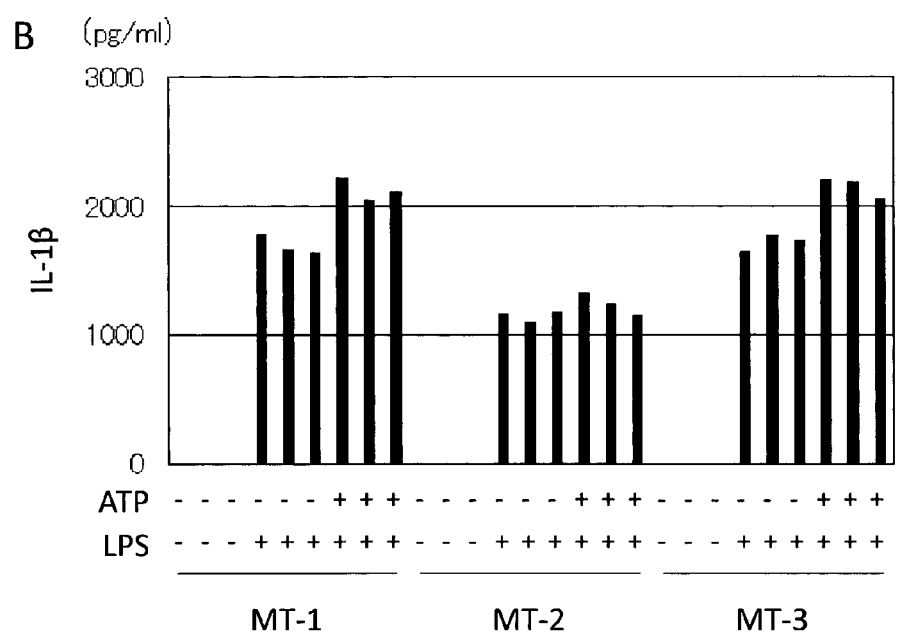

The iPS cells-derived macrophages obtained by the above method were suspended in RPMI medium supplemented with 10% FCS and divided into 3 groups, that is, (1) non-addition group, (2) a group in which LPS (Lipopolysaccharide) was added to the medium at 1 μg/ml and the macrophages were then cultured for 4 hours, and (3) a group in which LPS (Lipopolysaccharide) was added to the medium at 1 μg/ml and the macrophages were then cultured for 4 hours, followed by adding ATP (Adenosine triphosphate) to the medium at 1 mM and then culturing the macrophages for 30 minutes. Thereafter, the culture supernatant in each group was recovered. The recovered culture supernatant was subjected to flow cytometry to measure the concentration of IL-1β using Human Th1/Th2 11plex Kit (BMS) according to the attached protocol (FIG. 2). The measurement was carried out 3 times in the same manner for each group. As a result, it was observed that a larger amount of IL-1β was secreted by LPS stimulation, from the macrophages having the mutant NLRP3 gene than from the macrophages having wild-type NLRP3 gene. The stimulation with ATP did not cause any change.

Intracellular Distribution of ASC

Figure 3:
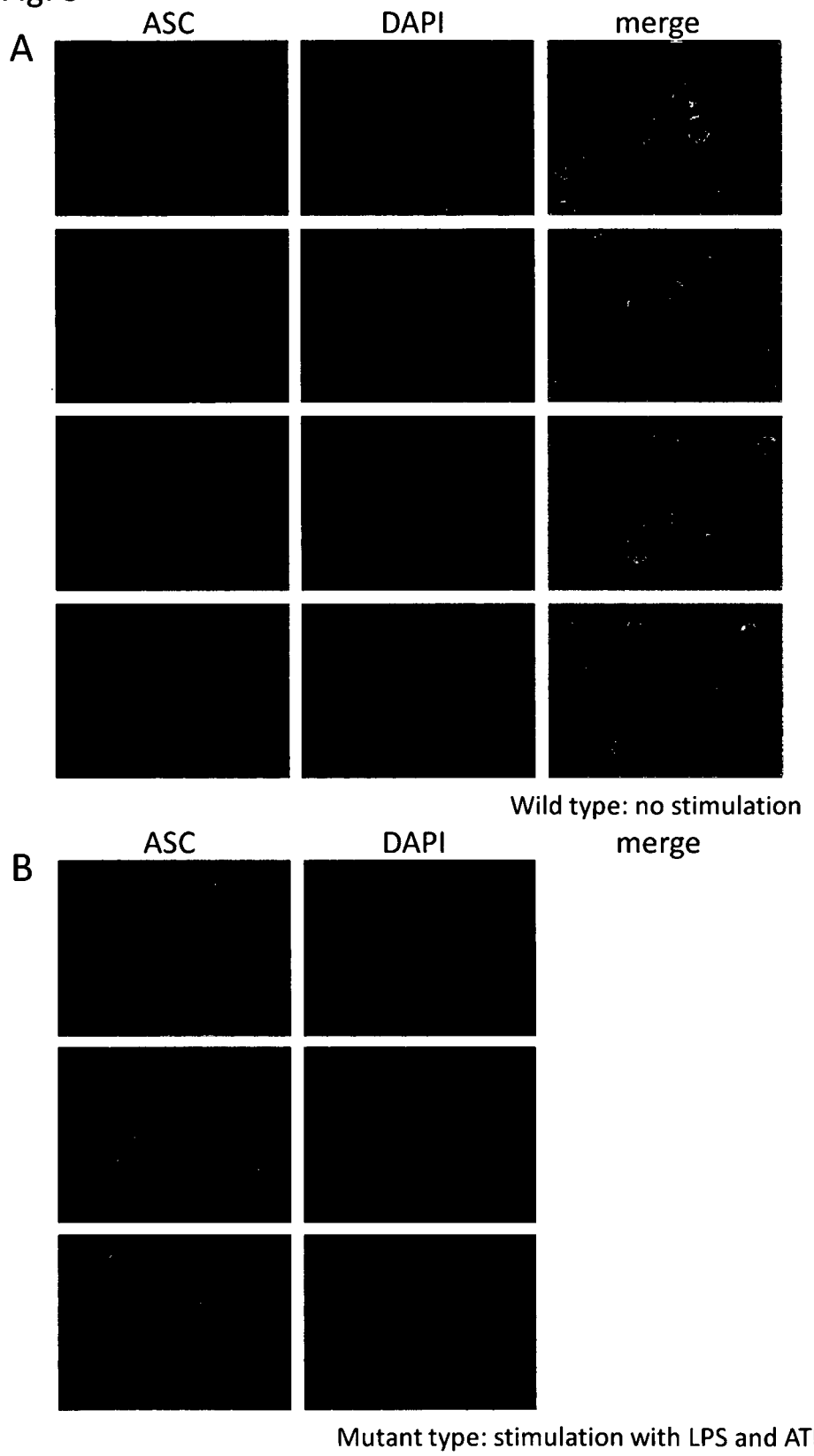
FIG. 3 shows stained images of ASC (left column), stained images by DAPI (middle column) and their superimposed images (right column) in iPS cells-derived macrophages having (A) wild-type NLRP3 gene and (B) mutant NLRP3 gene (photograph). Aggregation of ASC is observed only in cells of the mutant type.

LPS (Lipopolysaccharide) was added to a culture medium at 1 μg/ml and macrophages derived from iPS cells having mutant NLRP3 gene were cultured therein for 24 hours, followed by adding ATP (Adenosine triphosphate) to the medium at 1 mM and then culturing the macrophages for 30 minutes. Immunostaining was carried out to measure the intracellular distribution of ASC (Apoptotic speck-like protein containing a CARD) using an anti-ASC antibody. As a result, a large number of cells presenting aggregation of ASC, which is an index of activation of inflammasomes composed of NLRP3, ASC and caspase-1, were observed in the LPS/ATP-stimulated group (FIG. 3B). On the other hand, in macrophages derived from iPS cells having wild-type NLRP3 gene, which macrophages were not stimulated with LPS and ATP, ASC was distributed throughout the cell and aggregation of ASC was not observed (FIG. 3A). From the above results, it was found that, in macrophages derived from iPS cells having mutant NLRP3 gene, inflammasomes are activated by stimulation with LPS and ATP.

Evaluation of Drug Effects

Figure 4:
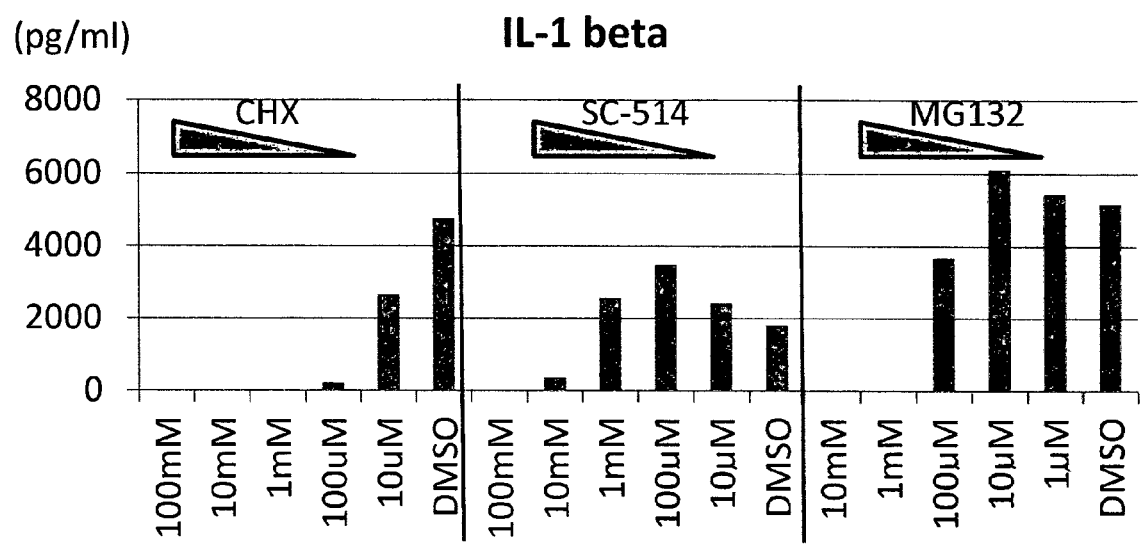
FIG. 4 shows the amount of IL-1β secretion in macrophages derived from iPS cells having mutant NLRP3 gene in the presence of each concentration of cycloheximide (left), SC-514 (middle) and MG132 (right), respectively.

The macrophage MT-1 induced from iPS cells as described above was added with each concentration of cycloheximide (CHX) (Sigma), SC-514 (Tocris) or MG132 (Calbiochem) and cultured for two hours, and the medium was replaced with a medium containing each drug and LPS (1 μg/ml), and culture was performed for another four hours, followed by measurement of the amount of IL-1β secretion using Human Th1/Th2 11plex Kit (FIG. 4). It was confirmed that NF-κB inhibitor SC-514 and MG132 inhibited IL-1β secretion in a dose dependent manner, as in the case of CHX used as a control.

The macrophage MT-1 induced from iPS cells as described above was added with 100 ng/ml of interleukin 1 receptor antagonist (IL-1Ra) (R&D Systems), 12 μM of Bay11-7028 (Sigma), 50 μM of CA074Me (Calbiochem) or 10 μM of Parthenolide (Parth) and cultured for two hours, and the medium was replaced with a medium containing each drug and LPS (1 μg/ml), and culture was performed for another four hours, followed by measurement of the amount of secretion of IL-1β (FIG. 5A), IL-8 (FIG. 5B), IL-6 (FIG. 5C) using Human Th1/Th2 11plex Kit. It was found that the secretion amount of the three types of interleukins did not change with the addition of IL-1 Ra whereas the secretion amount of the three types of interleukins was inhibited with Bay11-7028 and Parth. On the other hand, CA074Me specifically inhibited the secretion amount of IL-1β. These results show that drug effects can be evaluated by using macrophages induced from iPS cells derived from the CINCA syndrome patient.

INDUSTRIAL APPLICABILITY

The method of the present invention is useful for screening a drug such as a therapeutic agent for asbestosis, Alzheimer's disease, type 2 diabetes, atherosclerotic cardiovascular disease, gout, or cryopyrin-associated periodic syndrome.

In this specification, the test substance can be provided as the drug candidate compound.

While the present invention has been described with emphasis on preferred embodiments, it is obvious to those skilled in the art that the preferred embodiments can be modified. For example, the motivation to generate a certain drug through the combination or the synthesis of the screened drug candidate compound with other chemical compound is not precluded under the present invention. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

What is claimed is:

1. A method for obtaining a drug for suppressing inflammasome induction of IL-1β production and secretion, comprising the steps of:
(a) contacting a test substance with LPS-stimulated macrophages derived from induced pluripotent stem (iPS) cells having mutant NLRP3 genes;
(b) measuring the amount of IL-1β secretion from the macrophages after step (a);
(c) selecting as a drug for suppressing inflammasome induction of IL-1β production and secretion the test substance which makes the amount of secretion measured in step (b) equivalent to or less than the amount of IL-1β secretion from LPS-stimulated macrophages derived from iPS cells having wild-type NLRP3 genes; and
(d) obtaining the drug for suppressing inflammasome induction of IL-1β production and secretion based upon the selection in step (c),
wherein said mutant NLRP3 genes have a nucleotide substitution which replaces adenine at position 1709 with guanine counted from the translation initiation codon, a nucleotide substitution which replaces cytosine at position 1043 with thymine counted from the translation initiation codon, or a nucleotide substitution which replaces guanine at position 587 with adenine counted from the translation initiation codon, wherein said iPS cells having mutant NLRP3 genes and said iPS cells having wild-type NLRP3 genes are iPS cells derived from the same individual.

2. A method for obtaining a drug for suppressing inflammasome induction of IL-1β production and secretion, comprising the steps of:
(a) contacting a test substance with LPS-stimulated macrophages derived from iPS cells having mutant NLRP3 genes and with LPS-stimulated macrophages derived from iPS cells having wild-type NLRP3 genes;
(b) measuring the amount of IL-1βsecretion from the respective macrophages after step (a);
(c) selecting as a drug for suppressing inflammasome induction of IL-1β production and secretion the test substance which makes the amount of IL- β secretion from the macrophages derived from iPS cells having mutant NLRP3 genes measured in step (b) less than the amount of IL-1β secretion from macrophages derived from iPS cells having mutant NLRP3 genes which are stimulated with LPS but not contacted with the test substance, and the amount of IL-1β secretion from the macrophages derived from iPS cells having wild-type NLRP3 genes measured in step (b) is equivalent to the amount of IL-1β secretion from macrophages derived from iPS cell having wild-type NLRP3 genes which are stimulated with LPS but not contacted with the test substance; and
(d) obtaining the drug for suppressing inflammasome induction of IL-1β production and secretion based upon the selection of step (c),
wherein said mutant NLRP3 genes have a nucleotide substitution which replaces adenine at position 1709 with guanine counted from the translation initiation codon, a nucleotide substitution which replaces cytosine at position 1043 with thymine counted from the translation initiation codon, or a nucleotide substitution which replaces guanine at position 587 with adenine counted from the translation initiation codon, wherein said iPS cells having mutant NLRP3 genes and said iPS cells having wild-type NLRP3 genes are iPS cells derived from the same individual.

3. The method according to claim 1, wherein said drug for suppressing inflammasome induction of IL-1β production and secretion is a therapeutic agent for asbestosis, Alzheimer's disease, type 2 diabetes, atherosclerotic cardiovascular disease, gout, or cryopyrin-associated periodic syndrome.

4. The method according to claim 1, wherein macrophages derived from iPS cells having wild-type NLRP3 genes are further stimulated with ATP.

5. The method according to claim 2, wherein said drug for suppressing inflammasome induction of IL-1β production and secretion is a therapeutic agent for asbestosis, Alzheimer's disease, type 2 diabetes, atherosclerotic cardiovascular disease, gout, or cryopyrin-associated periodic syndrome.

6. The method according to claim 2, wherein macrophages derived from iPS cells having wild-type NLRP3 genes are further stimulated with ATP.

7. The method according to claim 1, wherein said wild-type and mutant NLRP3 genes are from a human.

8. The method according to claim 1, wherein said wild-type NLRP3 gene has a nucleotide sequence selected from the group consisting of SEQ ID NO: 1, SEQ ID NO: 2, SEQ ID NO: 3, SEQ ID NO: 4, and SEQ ID NO: 5.

9. The method according to claim 2, wherein said wild-type and mutant NLRP3 genes are from a human.

10. The method according to claim 2, wherein said wild-type NLRP3 gene has a nucleotide sequence selected from the group consisting of SEQ ID NO: 1, SEQ ID NO: 2, SEQ ID NO: 3, SEQ ID NO: 4, and SEQ ID NO: 5.

11. The method according to claim 1, wherein said individual suffers from asbestosis, Alzheimer's disease, type 2 diabetes, atherosclerotic cardiovascular disease, gout, or cryopyrin-associated periodic syndrome.

12. The method according to claim 2, wherein said individual suffers from asbestosis, Alzheimer's disease, type 2 diabetes, atherosclerotic cardiovascular disease, gout, or cryopyrin-associated periodic syndrome.

* * * * *

UNITED STATES PATENT AND TRADEMARK OFFICE
CERTIFICATE OF CORRECTION

PATENT NO. : 9,557,321 B2
APPLICATION NO. : 13/885950
DATED : January 31, 2017
INVENTOR(S) : Tatsutoshi Nakahata et al.

It is certified that error appears in the above-identified patent and that said Letters Patent is hereby corrected as shown below:

On the Title Page

In Column 2 (item (56)) at Line 14, Under Other Publications, change "Urticariam" to --Urticaria--.

In Column 2 (item (56)) at Line 33, Under Other Publications, change "inflamasomes" to --inflammasomes--.

In Column 2 (item (56)) at Line 33, Under Other Publications, change "requires" to --required--.

In Column 2 (item (56)) at Line 38, Under Other Publications, change "Cellls," to --Cells,--.

In the Specification

In Column 4 at Line 66, Change "$NM_{13}$ 004895" to --NM_004895--.

In Column 4 at Lines 66-67, Change "$NM_{13}$ 183395" to --NM_183395--.

In Column 4 at Line 67, Change "$NM_{13}$ 001079821" to --NM_001079821--.

In Column 5 at Line 1, Change "$NM_{13}$ 001127462" to --NM_001127462--.

In Column 7 at Line 23, Change "(R L." to --(R. L.--.

In Column 7 at Line 38, Change "(3-" to --β- --.

In Column 8 at Line 53, Change "derived;" to --derived,--.

In Column 9 at Lines 31-32, Change "3'-thiolglycerol;" to --3'-thioglycerol;--.

Signed and Sealed this
Fifteenth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,557,321 B2

In Column 10 at Line 58, Change "$NM_{13}$ 013258" to --NM_013258--.

In Column 11 at Line 21, Change "of" to --of:--.

In Column 14 at Line 36, Change "IL-1 Ra" to --IL-1Ra--.

In the Claims

In Column 69 at Line 57, In Claim 2, change "IL-1βsecretion" to --IL-1β secretion--.

In Column 69 at Line 61, In Claim 2, change "IL- β" to --IL-1β--.

SEQUENCE LISTING

<160> NUMBER OF SEQ ID NOS: 17

<210> SEQ ID NO 1
<211> LENGTH: 3111
<212> TYPE: DNA
<213> ORGANISM: Homo sapiens

<400> SEQUENCE: 1

| | | | | | |
|---|---|---|---|---|---|
| atgaagatgg | caagcacccg | ctgcaagctg | gccaggtacc | tggaggacct | ggaggatgtg | 60 |
| gacttgaaga | aatttaagat | gcacttagag | gactatcctc | cccagaaggg | ctgcatcccc | 120 |
| ctcccgaggg | gtcagacaga | gaaggcagac | catgtggatc | tagccacgct | aatgatcgac | 180 |
| ttcaatgggg | aggagaaggc | gtgggccatg | gccgtgtgga | tcttcgctgc | gatcaacagg | 240 |
| agagaccttt | atgagaaagc | aaaaagagat | gagccgaagt | ggggttcaga | taatgcacgt | 300 |
| gtttcgaatc | ccactgtgat | atgccaggaa | gacagcattg | aagaggagtg | gatgggttta | 360 |
| ctggagtacc | tttcgagaat | ctctatttgt | aaaatgaaga | aagattaccg | taagaagtac | 420 |
| agaaagtacg | tgagaagcag | attccagtgc | attgaagaca | ggaatgcccg | tctgggtgag | 480 |
| agtgtgagcc | tcaacaaacg | ctacacacga | ctgcgtctca | tcaaggagca | ccggagccag | 540 |
| caggagaggg | agcaggagct | tctggccatc | ggcaagacca | agacgtgtga | gagccccgtg | 600 |
| agtcccatta | agatggagtt | gctgtttgac | cccgatgatg | agcattctga | gcctgtgcac | 660 |
| accgtggtgt | tccagggggc | ggcagggatt | gggaaaacaa | tcctggccag | gaagatgatg | 720 |
| ttggactggg | cgtcggggac | actctaccaa | gacaggtttg | actatctgtt | ctatatccac | 780 |
| tgtcgggagg | tgagccttgt | gacacagagg | agcctggggg | acctgatcat | gagctgctgc | 840 |
| cccgacccaa | acccacccat | ccacaagatc | gtgagaaaac | cctccagaat | cctcttcctc | 900 |
| atggacggct | tcgatgagct | gcaaggtgcc | tttgacgagc | acataggacc | gctctgcact | 960 |
| gactggcaga | aggccgagcg | gggagacatt | ctcctgagca | gcctcatcag | aaagaagctg | 1020 |
| cttcccgagg | cctctctgct | catcaccacg | agacctgtgg | ccctggagaa | actgcagcac | 1080 |
| ttgctggacc | atcctcggca | tgtggagatc | ctgggtttct | ccgaggccaa | aaggaaagag | 1140 |
| tacttcttca | agtacttctc | tgatgaggcc | caagccaggg | cagccttcag | tctgattcag | 1200 |
| gagaacgagg | tcctcttcac | catgtgcttc | atcccctgg | tctgctggat | cgtgtgcact | 1260 |
| ggactgaaac | agcagatgga | gagtggcaag | agccttgccc | agacatccaa | gaccaccacc | 1320 |
| gcggtgtacg | tcttcttcct | ttccagttg | ctgcagcccc | ggggagggag | ccaggagcac | 1380 |
| ggcctctgcg | cccacctctg | ggggctctgc | tctttggctg | cagatggaat | ctggaaccag | 1440 |
| aaaatcctgt | ttgaggagtc | cgacctcagg | aatcatggac | tgcagaaggc | ggatgtgtct | 1500 |
| gctttcctga | ggatgaacct | gttccaaaag | gaagtggact | gcgagaagtt | ctacagcttc | 1560 |
| atccacatga | ctttccagga | gttctttgcc | gccatgtact | acctgctgga | agaggaaaag | 1620 |
| gaaggaagga | cgaacgttcc | agggagtcgt | ttgaagcttc | ccagccgaga | cgtgacagtc | 1680 |
| cttctggaaa | actatggcaa | attcgaaaag | gggtatttga | tttttgttgt | acgtttcctc | 1740 |
| tttggcctgg | taaccagga | gaggacctcc | tacttggaga | agaaattaag | ttgcaagatc | 1800 |
| tctcagcaaa | tcaggctgga | gctgctgaaa | tggattgaag | tgaaagccaa | agctaaaaag | 1860 |
| ctgcagatcc | agcccagcca | gctggaattg | ttctactgtt | tgtacgagat | gcaggaggag | 1920 |
| gacttcgtgc | aaagggccat | ggactatttc | cccaagattg | agatcaatct | ctccaccaga | 1980 |
| atggaccaca | tggtttcttc | cttttgcatt | gagaactgtc | atcgggtgga | gtcactgtcc | 2040 |
| ctggggtttc | tccataacat | gcccaaggag | gaagaggagg | aggaaaagga | aggccgacac | 2100 |

```
cttgatatgg tgcagtgtgt cctcccaagc tcctctcatg ctgcctgttc tcatggattg    2160
gtgaacagcc acctcacttc cagttttgc cggggcctct tttcagttct gagcaccagc     2220
cagagtctaa ctgaattgga cctcagtgac aattctctgg gggacccagg atgagagtg     2280 ttgtgtgaaa cgctccagca tcctggctgt aacattcgga gattgtggtt ggggcgctgt    2340
ggcctctcgc atgagtgctg cttcgacatc tccttggtcc tcagcagcaa ccagaagctg    2400
gtggagctgg acctgagtga caacgccctc ggtgacttcg gaatcagact tctgtgtgtg    2460
ggactgaagc acctgttgtg caatctgaag aagctctggt tggtcagctg ctgcctcaca    2520
tcagcatgtt gtcaggatct tgcatcagta ttgagcacca gccattccct gaccagactc    2580
tatgtggggg agaatgcctt gggagactca ggagtcgcaa ttttatgtga aaaagccaag    2640
aatccacagt gtaacctgca gaaactgggg ttggtgaatt ctggccttac gtcagtctgt    2700
tgttcagctt tgtcctcggt actcagcact aatcagaatc tcacgcacct ttacctgcga    2760
ggcaacactc tcggagacaa ggggatcaaa ctactctgtg agggactctt gcaccccgac    2820
tgcaagcttc aggtgttgga attagacaac tgcaacctca cgtcacactg ctgctgggat    2880
ctttccacac ttctgacctc cagccagagc tgcgaaagc tgagcctggg caacaatgac     2940
ctgggcgacc tgggggtcat gatgttctgt gaagtgctga acagcagag ctgcctcctg     3000 cagaacctgg ggttgtctga aatgtatttc aattatgaga caaaaagtgc gttagaaaca    3060
cttcaagaag aaaagcctga gctgaccgtc gtctttgagc cttcttggta g             3111

<210> SEQ ID NO 2
<211> LENGTH: 2769
<212> TYPE: DNA
<213> ORGANISM: Homo sapiens

<400> SEQUENCE: 2
atgaagatgg caagcacccg ctgcaagctg gccaggtacc tggaggacct ggaggatgtg      60
gacttgaaga aatttaagat gcacttagag gactatcctc cccagaaggg ctgcatcccc     120
ctcccgaggg gtcagacaga gaaggcagac catgtggatc tagccacgct aatgatcgac     180
ttcaatgggg aggagaaggc gtgggccatg gccgtgtgga tcttcgctgc gatcaacagg     240
agagaccttt atgagaaagc aaaaagagat gagccgaagt ggggttcaga taatgcacgt     300
gtttcgaatc ccactgtgat atgccaggaa gacagcattg aagaggagtg gatgggttta    360
ctggagtacc tttcgagaat ctctatttgt aaaatgaaga aagattaccg taagaagtac    420
agaaagtacg tgaagaagcag attccagtgc attgaagaca ggaatgcccg tctgggtgag   480
agtgtgagcc tcaacaaacg ctacacacga ctgcgtctca tcaaggagca ccggagccag    540
caggagaggg agcaggagct tctggccatc ggcaagacca agacgtgtga agcccccgtg     600
agtcccatta gatggagtt gctgtttgac cccgatgatg agcattctga gcctgtgcac      660
accgtggtgt tccaggggc ggcagggatt gggaaaacaa tcctggccag aagatgatg      720 ttggactggg cgtcggggac actctaccaa gacaggtttg actatctgtt ctatatccac    780
tgtcgggagg tgagccttgt gacacagagg agcctggggg acctgatcat gagctgctgc    840
cccgacccaa acccacccat ccacaagatc gtgagaaaac cctccagaat cctcttcctc    900
atggacggct tcgatgagct gcaaggtgcc tttgacgagc acataggacc gctctgcact    960
gactggcaga aggccgagcg gggagacatt tccctgagca gcctcatcag aaagaagctg    1020
cttcccgagg cctctctgct catcaccacg agacctgtgg ccctggagaa actgcagcac   1080
```

```
ttgctggacc atcctcggca tgtggagatc ctgggtttct ccgaggccaa aaggaaagag   1140
tacttcttca agtacttctc tgatgaggcc caagccaggg cagccttcag tctgattcag   1200
gagaacgagg tcctcttcac catgtgcttc atcccctgg  tctgctggat cgtgtgcact   1260
ggactgaaac agcagatgga gagtggcaag agccttgccc agacatccaa gaccaccacc   1320
gcggtgtacg tcttcttcct ttccagtttg ctgcagcccc ggggagggag ccaggagcac   1380
ggcctctgcg cccacctctg ggggctctgc tctttggctg cagatggaat ctggaaccag   1440
aaaatcctgt ttgaggagtc cgacctcagg aatcatggac tgcagaaggc ggatgtgtct   1500
gctttcctga ggatgaacct gttccaaaag gaagtggact gcgagaagtt ctacagcttc   1560
atccacatga ctttccagga gttctttgcc gccatgtact acctgctgga agaggaaaag   1620
gaaggaagga cgaacgttcc agggagtcgt tgaagcttc  ccagccgaga cgtgacagtc   1680
cttctggaaa actatggcaa attcgaaaag gggtatttga ttttttgttgt acgtttcctc   1740 tttggcctgg taaaccagga gaggacctcc tacttggaga agaaattaag ttgcaagatc   1800
tctcagcaaa tcaggctgga gctgctgaaa tggattgaag tgaaagccaa agctaaaaag   1860
ctgcagatcc agcccagcca gctggaattg ttctactgtt tgtacgagat gcaggaggag   1920
gacttcgtgc aaagggccat ggactatttc cccaagattg agatcaatct ctccaccaga   1980
atggaccaca tggtttcttc ctttttgcatt gagaactgtc atcgggtgga gtcactgtcc   2040
ctggggtttc tccataacat gcccaaggag gaagaggagg aggaaaagga aggccgacac   2100
cttgatatgg tgcagtgtgt cctcccaagc tcctctcatg ctgcctgttc tcatgggttg   2160
gggcgctgtg gcctctcgca tgagtgctgc ttcgacatct ccttggtcct cagcagcaac   2220
cagaagctgg tggagctgga cctgagtgac aacgccctcg gtgacttcgg aatcagactt   2280
ctgtgtgtgg gactgaagca cctgttgtgc aatctgaaga agctctggtt ggtgaattct   2340
ggccttacgt cagtctgttg ttcagctttg tcctcggtac tcagcactaa tcagaatctc   2400
acgcaccttt acctgcgagg caacactctc ggagacaagg ggatcaaact actctgtgag   2460
ggactcttgc accccgactg caagcttcag gtgttggaat agacaactg  caacctcacg   2520 tcacactgct gctgggatct ttccacactt ctgacctcca gccagagcct gcgaaagctg   2580
agcctgggca acaatgacct gggcgacctg ggggtcatga tgttctgtga agtgctgaaa   2640
cagcagagct gcctcctgca gaacctgggg ttgtctgaaa tgtatttcaa ttatgagaca   2700
aaaagtgcgt tagaaacact tcaagaagaa aagcctgagc tgaccgtcgt cttttgagcct   2760 tcttggtag                                                           2769
```

<210> SEQ ID NO 3
<211> LENGTH: 3111
<212> TYPE: DNA
<213> ORGANISM: Homo sapiens

<400> SEQUENCE: 3

```
atgaagatgg caagcacccg ctgcaagctg gccaggtacc tggaggacct ggaggatgtg    60
gacttgaaga aatttaagat gcacttagag gactatcctc cccagaaggg ctgcatcccc   120
ctcccgaggg tcagacagag aaggcagac  catgtggatc tagccacgct aatgatcgac   180
ttcaatgggg aggagaaggc gtgggccatg gccgtgtgga tcttcgctgc gatcaacagg   240
agagaccttt atgagaaagc aaaaagagat gagccgaagt ggggttcaga taatgcacgt   300
gtttcgaatc ccactgtgat atgccaggaa gacagcattg aagaggagtg gatgggttta   360
ctggagtacc tttcgagaat ctctatttgt aaaatgaaga agattaccg  taagaagtac   420
```

| | |
|---|---|
| agaaagtacg tgagaagcag attccagtgc attgaagaca ggaatgcccg tctgggtgag | 480 |
| agtgtgagcc tcaacaaacg ctacacacga ctgcgtctca tcaaggagca ccggagccag | 540 |
| caggagaggg agcaggagct tctggccatc ggcaagacca agacgtgtga gagcccgtg | 600 |
| agtcccatta agatggagtt gctgtttgac cccgatgatg agcattctga gcctgtgcac | 660 |
| accgtggtgt tccagggggc ggcagggatt gggaaaacaa tcctggccag gaagatgatg | 720 |
| ttggactggg cgtcggggac actctaccaa gacaggtttg actatctgtt ctatatccac | 780 |
| tgtcgggagg tgagccttgt gacacagagg agcctggggg acctgatcat gagctgctgc | 840 |
| cccgacccaa acccacccat ccacaagatc gtgagaaaac cctccagaat cctcttcctc | 900 |
| atggacggct tcgatgagct gcaaggtgcc tttgacgagc acataggacc gctctgcact | 960 |
| gactggcaga aggccgagcg gggagacatt ctcctgagca gcctcatcag aaagaagctg | 1020 |
| cttcccgagg cctctctgct catcaccacg agacctgtgg ccctggagaa actgcagcac | 1080 |
| ttgctggacc atcctcggca tgtggagatc ctgggtttct ccgaggccaa aaggaaagag | 1140 |
| tacttcttca agtacttctc tgatgaggcc caagccaggg cagccttcag tctgattcag | 1200 |
| gagaacgagg tcctcttcac catgtgcttc atcccctgg tctgctggat cgtgtgcact | 1260 |
| ggactgaaac agcagatgga gagtggcaag agccttgccc agacatccaa gaccaccacc | 1320 |
| gcggtgtacg tcttcttcct ttccagtttg ctgcagcccc ggggaggag ccaggagcac | 1380 |
| ggcctctgcg cccacctctg ggggctctgc tctttggctg cagatggaat ctggaaccag | 1440 |
| aaaatcctgt ttgaggagtc cgacctcagg aatcatggac tgcagaaggc ggatgtgtct | 1500 |
| gctttcctga ggatgaacct gttccaaaag gaagtggact gcgagaagtt ctacagcttc | 1560 |
| atccacatga ctttccagga gttctttgcc gccatgtact acctgctgga agaggaaaag | 1620 |
| gaaggaagga cgaacgttcc agggagtcgt ttgaagcttc ccagccgaga cgtgacagtc | 1680 |
| cttctggaaa actatggcaa attcgaaaag gggtatttga tttttgttgt acgtttcctc | 1740 |
| tttggcctgg taaaccagga gaggacctcc tacttggaga agaaattaag ttgcaagatc | 1800 |
| tctcagcaaa tcaggctgga gctgctgaaa tggattgaag tgaaagccaa agctaaaaag | 1860 |
| ctgcagatcc agcccagcca gctggaattg ttctactgtt tgtacgagat gcaggaggag | 1920 |
| gacttcgtgc aaagggccat ggactatttc cccaagattg agatcaatct ctccaccaga | 1980 |
| atggaccaca tggtttcttc cttttgcatt gagaactgtc atcgggtgga gtcactgtcc | 2040 |
| ctggggtttc tccataacat gcccaaggag gaagaggagg aggaaaagga aggccgacac | 2100 |
| cttgatatgt gcagtgtgt cctcccaagc tcctctcatg ctgcctgttc tcatggattg | 2160 |
| gtgaacagcc acctcacttc cagttttttgc cggggcctct tttcagttct gagcaccagc | 2220 |
| cagagtctaa ctgaattgga cctcagtgac aattctctgg ggacccagg gatgagagtg | 2280 |
| ttgtgtgaaa cgctccagca tcctggctgt aacattcgga gattgtggtt ggggcgctgt | 2340 |
| ggcctctcgc atgagtgctg cttcgacatc tccttggtcc tcagcagcaa ccagaagctg | 2400 |
| gtggagctgg acctgagtga caacgccctc ggtgacttcg aatcagact tctgtgtgtg | 2460 |
| ggactgaagc acctgttgtg caatctgaag aagctctggt tggtcagctg ctgcctcaca | 2520 |
| tcagcatgtt gtcaggatct tgcatcagta ttgagcacca gcattccct gaccagactc | 2580 |
| tatgtggggg agaatgcctt gggagactca ggagtcgcaa ttttatgtga aaaagccaag | 2640 |
| aatccacagt gtaacctgca gaaactgggg ttggtgaatt ctggccttac gtcagtctgt | 2700 |
| tgttcagctt tgtcctcggt actcagcact aatcagaatc tcacgcacct ttacctgcga | 2760 |

| | |
|---|---|
| ggcaacactc tcggagacaa ggggatcaaa ctactctgtg agggactctt gcaccccgac | 2820 |
| tgcaagcttc aggtgttgga attagacaac tgcaacctca cgtcacactg ctgctgggat | 2880 |
| cttccacac ttctgacctc cagccagagc ctgcgaaagc tgagcctggg caacaatgac | 2940 |
| ctgggcgacc tggggtcat gatgttctgt gaagtgctga acagcagag ctgcctcctg | 3000 |
| cagaacctgg ggttgtctga aatgtatttc aattatgaga caaaaagtgc gttagaaaca | 3060 |
| cttcaagaag aaaagcctga gctgaccgtc gtctttgagc cttcttggta g | 3111 |

```
<210> SEQ ID NO 4
<211> LENGTH: 2940
<212> TYPE: DNA
<213> ORGANISM: Homo sapiens

<400> SEQUENCE: 4
```

| | |
|---|---|
| atgaagatgg caagcacccg ctgcaagctg gccaggtacc tggaggacct ggaggatgtg | 60 |
| gacttgaaga aatttaagat gcacttagag gactatcctc cccagaaggg ctgcatcccc | 120 |
| ctcccgaggg gtcagacaga gaaggcagac catgtggatc tagccacgct aatgatcgac | 180 |
| ttcaatgggg aggagaaggc gtgggccatg ccgtgtgga tcttcgctgc gatcaacagg | 240 |
| agagaccttt atgagaaagc aaaaagagat gagccgaagt gggggttcaga taatgcacgt | 300 |
| gtttcgaatc ccactgtgat atgccaggaa gacagcattg aagaggagtg gatgggttta | 360 |
| ctggagtacc tttcgagaat ctctatttgt aaaatgaaga aagattaccg taagaagtac | 420 |
| agaaagtacg tgagaagcag attccagtgc attgaagaca ggaatgcccg tctgggtgag | 480 |
| agtgtgagcc tcaacaaacg ctacacacga ctgcgtctca tcaaggagca ccggagccag | 540 |
| caggagaggg agcaggagct tctggccatc ggcaagacca agacgtgtga gagccccgtg | 600 |
| agtcccatta gatggagtt gctgtttgac cccgatgatg agcattctga gcctgtgcac | 660 |
| accgtggtgt ccaggggggc ggcagggatt gggaaaacaa tcctggccag gaagatgatg | 720 |
| ttggactggg cgtcggggac actctaccaa gacaggtttg actatctgtt ctatatccac | 780 |
| tgtcgggagg tgagccttgt gacacagagg agcctggggg acctgatcat gagctgctgc | 840 |
| cccgacccaa acccacccat ccacaagatc gtgagaaaac cctccagaat cctcttcctc | 900 |
| atggacggct tcgatgagct gcaaggtgcc tttgacgagc ataggacc gctctgcact | 960 |
| gactggcaga aggccgagcg gggagacatt ctcctgagca gcctcatcag aaagaagctg | 1020 |
| cttcccgagg cctctctgct catcaccacg agacctgtgg ccctggagaa actgcagcac | 1080 |
| ttgctggacc atcctcggca tgtggagatc ctgggtttct ccgaggccaa aaggaaagag | 1140 |
| tacttcttca agtacttctc tgatgaggcc caagccaggg cagccttcag tctgattcag | 1200 |
| gagaacgagg tcctcttcac catgtgcttc atccccctgg tctgctggat cgtgtgcact | 1260 |
| ggactgaaaac agcagatgga gagtggcaag agccttgccc agacatccaa gaccaccacc | 1320 |
| gcggtgtacg tcttcttcct ttccagttg ctgcagcccc ggggaggggag ccaggagcac | 1380 |
| ggcctctgcg cccacctctg ggggctctgc tctttggctg cagatggaat ctggaaccag | 1440 |
| aaaatcctgt ttgaggagtc cgacctcagg aatcatggac tgcagaaggc ggatgtgtct | 1500 |
| gctttcctga ggatgaacct gttccaaaag gaagtggact cgagaagtt ctacagcttc | 1560 |
| atccacatga ctttccagga gttctttgcc gccatgtact acctgctgga gaggaaaag | 1620 |
| gaaggaagga cgaacgttcc agggagtcgt tgaagcttc ccagccgaga cgtgacagtc | 1680 |
| cttctgaaaa actatggcaa attcgaaaag gggtatttga ttttgttgt acgtttcctc | 1740 |
| tttggcctgg taaaccagga gaggacctcc tacttggaga agaaattaag ttgcaagatc | 1800 |

-continued

```
tctcagcaaa tcaggctgga gctgctgaaa tggattgaag tgaaagccaa agctaaaaag    1860
ctgcagatcc agcccagcca gctggaattg ttctactgtt tgtacgagat gcaggaggag    1920
gacttcgtgc aaagggccat ggactatttc cccaagattg agatcaatct ctccaccaga    1980
atggaccaca tggtttcttc cttttgcatt gagaactgtc atcgggtgga gtcactgtcc    2040
ctggggtttc tccataacat gcccaaggag gaagaggagg aggaaaagga aggccgacac    2100
cttgatatgg tgcagtgtgt cctcccaagc tcctctcatg ctgcctgttc tcatggattg    2160
gtgaacagcc acctcacttc cagttttgc cggggcctct tttcagttct gagcaccagc    2220
cagagtctaa ctgaattgga cctcagtgac aattctctgg gggacccagg gatgagagtg    2280
ttgtgtgaaa cgctccagca tcctggctgt aacattcgga gattgtggtt ggggcgctgt    2340
ggcctctcgc atgagtgctg cttcgacatc tccttggtcc tcagcagcaa ccagaagctg    2400
gtggagctgg acctgagtga caacgccctc ggtgacttcg aatcagact tctgtgtgtg    2460 ggactgaagc acctgttgtg caatctgaag aagctctggt tggtgaattc tggccttacg    2520
tcagtctgtt gttcagcttt gtcctcggta ctcagcacta atcagaatct cacgcacctt    2580
tacctgcgag gcaacactct cggagacaag gggatcaaac tactctgtga gggactcttg    2640
caccccgact gcaagcttca ggtgttggaa ttagacaact gcaacctcac gtcacactgc    2700
tgctgggatc tttccacact tctgacctcc agcagagcc tgcgaaagct gagcctgggc    2760
aacaatgacc tgggcgacct gggggtcatg atgttctgtg aagtgctgaa acagcagagc    2820
tgcctcctgc agaacctggg gttgtctgaa atgtatttca attatgagac aaaaagtgcg    2880
ttagaaacac ttcaagaaga aaagcctgag ctgaccgtcg tctttgagcc ttcttggtag    2940
```

<210> SEQ ID NO 5
<211> LENGTH: 2940
<212> TYPE: DNA
<213> ORGANISM: Homo sapiens

<400> SEQUENCE: 5

```
atgaagatgg caagcacccg ctgcaagctg gccaggtacc tggaggacct ggaggatgtg      60
gacttgaaga aatttaagat gcacttagag actatcctc cccagaaggg ctgcatcccc     120
ctcccgaggg gtcagacaga aaggcagac catgtggatc tagccacgct aatgatcgac     180
ttcaatgggg aggagaaggc gtgggccatg gccgtgtgga tcttcgctgc gatcaacagg     240
agagaccttt atgagaaagc aaaaagagat gagccgaagt ggggttcaga taatgcacgt     300
gtttcgaatc ccactgtgat atgccaggaa gacagcattg aagaggagtg gatgggttta     360
ctggagtacc tttcgagaat ctctatttgt aaaatgaaga agattaccg taagaagtac     420 agaaagtacg tgaaagcag attccagtgc attgaagaca ggaatgcccg tctgggtgag     480
agtgtgagcc tcaacaaacg ctacacacga ctgcgtctca tcaaggagca ccggagccag     540
caggagaggg agcaggagct tctggccatc ggcaagacca agacgtgtga agccccgtg     600 agtcccatta agatggagtt gctgtttgac cccgatgatg agcattctga gcctgtgcac     660
accgtggtgt tccaggggc ggcagggatt gggaaaacaa tcctggccag gaagatgatg     720
ttggactggg cgtcggggac actctaccaa gacaggtttg actatctgtt ctatatccac     780
tgtcgggagg tgagccttgt gacacagagg agcctggggg acctgatcat gagctgctgc    840
cccgacccaa acccacccat ccacaagatc gtgagaaaac cctccagaat cctcttcctc     900
atggacggct tcgatgagct gcaaggtgcc tttgacgagc acataggacc gctctgcact     960
```

```
gactggcaga aggccgagcg gggagacatt ctcctgagca gcctcatcag aaagaagctg    1020
cttcccgagg cctctctgct catcaccacg agacctgtgg ccctggagaa actgcagcac    1080
ttgctggacc atcctcggca tgtggagatc ctgggtttct ccgaggccaa aaggaaagag    1140
tacttcttca gtacttctc tgatgaggcc caagccaggg cagccttcag tctgattcag    1200
gagaacgagg tcctcttcac catgtgcttc atcccctgg tctgctggat cgtgtgcact    1260
ggactgaaac agcagatgga gagtggcaag agccttgccc agacatccaa gaccaccacc    1320
gcggtgtacg tcttcttcct ttccagtttg ctgcagcccc ggggagggag ccaggagcac    1380
ggcctctgcg cccacctctg ggggctctgc tctttggctg cagatggaat ctggaaccag    1440
aaaatcctgt ttgaggagtc cgacctcagg aatcatggac tgcagaaggc ggatgtgtct    1500
gctttcctga ggatgaacct gttccaaaag gaagtggact gcgagaagtt ctacagcttc    1560
atccacatga ctttccagga gttctttgcc gccatgtact acctgctgga gaggaaaag    1620 gaaggaagga cgaacgttcc agggagtcgt tgaagcttc ccagccgaga cgtgacagtc    1680
cttctggaaa actatggcaa attcgaaaag gggtatttga ttttgttgt acgtttcctc    1740 tttggcctgg taaccagga gaggacctcc tacttggaga agaaattaag ttgcaagatc    1800
tctcagcaaa tcaggctgga gctgctgaaa tggattgaag tgaaagccaa agctaaaaag    1860
ctgcagatcc agcccagcca gctggaattg ttctactgtt tgtacgagat gcaggaggag    1920
gacttcgtgc aaagggccat ggactatttc cccaagattg agatcaatct ctccaccaga    1980
atggaccaca tggttttcttc cttttgcatt gagaactgtc atcgggtgga gtcactgtcc    2040
ctggggtttc tccataacat gcccaaggag gaagaggagg aggaaaagga aggccgacac    2100
cttgatatgg tgcagtgtgt cctcccaagc tcctctcatg ctgcctgttc tcatgggttg    2160
gggcgctgtg gcctctcgca tgagtgctgc ttcgacatct ccttggtcct cagcagcaac    2220
cagaagctgg tggagctgga cctgagtgac aacgccctcg gtgacttcgg aatcagactt    2280
ctgtgtgtgg gactgaagca cctgttgtgc aatctgaaga agctctggtt ggtcagctgc    2340
tgcctcacat cagcatgttg tcaggatctt gcatcagtat tgagcaccag ccattccctg    2400
accagactct atgtggggga gaatgccttg ggagactcag gagtcgcaat tttatgtgaa    2460
aaagccaaga atccacagtg taacctgcag aaactggggt tggtgaattc tggccttacg    2520
tcagtctgtt gttcagcttt gtcctcggta ctcagcacta atcagaatct cacgcacctt    2580
tacctgcgag gcaacactct cggagacaag gggatcaaac tactctgtga gggactcttg    2640
caccccgact gcaagcttca ggtgttggaa ttagacaact gcaacctcac gtcacactgc    2700
tgctgggatc tttccacact tctgacctcc agccagagcc tgcgaaagct gagcctgggc    2760
aacaatgacc tgggcgacct gggggtcatg atgttctgtg aagtgctgaa acagcagagc    2820
tgcctcctgc agaacctggg gttgtctgaa atgtatttca attatgagac aaaaagtgcg    2880
ttagaaacac ttcaagaaga aaagcctgag ctgaccgtcg tctttgagcc ttcttggtag    2940
```

<210> SEQ ID NO 6
<211> LENGTH: 782
<212> TYPE: DNA
<213> ORGANISM: Homo sapiens

<400> SEQUENCE: 6

```
gtccaggttc cgccccggag ccgacttcct cctggtcggc ggctgcagcg gggtgagcgg      60
cggcagcggc cggggatcct ggagccatgg ggcgcgcgcg cgacgccatc ctggatgcgc     120 tggagaaccct gaccgccgag gagctcaaga agttcaagct gaagctgctg tcggtgccgc     180
```

-continued

```
tgcgcgaggg ctacgggcgc atcccgcggg gcgcgctgct gtccatggac gccttggacc    240
tcaccgacaa gctggtcagc ttctacctgg agacctacgg cgccgagctc accgctaacg    300
tgctgcgcga catgggcctg caggagatgg ccgggcagct gcaggcggcc acgcaccagg    360
gctctggagc cgcgccagct gggatccagg cccctcctca gtcggcagcc aagccaggcc    420
tgcactttat agaccagcac cgggctgcgc ttatcgcgag ggtcacaaac gttgagtggc    480
tgctggatgc tctgtacggg aaggtcctga cggatgagca gtaccaggca gtgcgggccg    540
agcccaccaa cccaagcaag atgcggaagc tcttcagttt cacaccagcc tggaactgga    600
cctgcaagga cttgctcctc caggcccta agggagtccca gtcctacctg gtggaggacc    660
tggagcggag ctgaggctcc ttcccagcaa cactccggtc agccctggc aatcccacca    720 aatcatcctg aatctgatct ttttatacac aatatacgaa aagccagctt gaaaaaaaa    780 aa                                                                   782
```

<210> SEQ ID NO 7
<211> LENGTH: 725
<212> TYPE: DNA
<213> ORGANISM: Homo sapiens

<400> SEQUENCE: 7

```
gtccaggttc cgccccggag ccgacttcct cctggtcggc ggctgcagcg gggtgagcgg     60
cggcagcggc cggggatcct ggagccatgg ggcgcgcgcg cgacgccatc ctggatgcgc    120
tggagaacct gaccgccgag gagctcaaga agttcaagct gaagctgctg tcggtgccgc    180
tgcgcgaggg ctacgggcgc atcccgcggg gcgcgctgct gtccatggac gccttggacc    240
tcaccgacaa gctggtcagc ttctacctgg agacctacgg cgccgagctc accgctaacg    300
tgctgcgcga catgggcctg caggagatgg ccgggcagct gcaggcggcc acgcaccagg    360
gcctgcactt tatagaccag caccgggctg cgcttatcgc gagggtcaca aacgttgagt    420
ggctgctgga tgctctgtac gggaaggtcc tgacggatga gcagtaccag gcagtgcggg    480
ccgagcccac caacccaagc aagatgcgga agctcttcag tttcacacca gcctggaact    540
ggacctgcaa ggacttgctc ctccaggccc taagggagtc ccagtcctac ctggtggagg    600
acctggagcg gagctgaggc tccttcccag caacactccg gtcagcccct ggcaatccca    660
ccaaatcatc ctgaatctga tctttttata cacaatatac gaaaagccag cttgaaaaaa    720
aaaaa                                                                725
```

<210> SEQ ID NO 8
<211> LENGTH: 3686
<212> TYPE: DNA
<213> ORGANISM: Mus musculus

<400> SEQUENCE: 8

```
agtcgggaaa caatgcgcct gcagatcgcg ctcccgcgtc gatcccggga gcgtcctggc     60
tgccgtgtgc gagcgaggcg gggggcgcgc gcacgggggg cgcgctcgtg agtgcggggc    120
cgcgcgctcg gtggcgcgca tgtgtgtgtg tgcgggctgc cgggcttccc cgagccggcg    180
gggagccgct ccgctccagg tggcgggcgg cgggagcgag gtgaggctgc gggtggcccg    240
ggcaggggtc cccaggggac tggcgggctg caaggctgca gactgccttc gagacagcgc    300 gccccgccc ggccctgctg tgccccgga gctgagctcc gggcggtgct ggcaaagttt    360
gctttgaact cgctcccctc agcctggtcg gcccgttgcg agctgccctg agcgagctga    420
```

```
ccccaggcca ggcttcccag gagcagggac cagggcgcgg gctgcaagct ggtgggcctg    480
gggagagacc agagccccgc agccagctgc agcgagggac tcggagccgc ctcttccctc    540
ggcgggcacc gcagtcagct cgtctccccc ttccctcccg cagggagcgg acatggactt    600
cgactcgtat cagcactatt tctacgacta tgactgcgga gaggatttct accgctccac    660
ggcgcccagc gaggacatct ggaagaaatt cgagctggtg ccgtcgcccc ccacgtcgcc    720
gccctggggc tccggtcccg cgccgtgga cccagcctct gggattaatc ccggggagcc    780
gtggcctgga gggggtgccg gggacgaggc ggaatctcgg ggccattcga aagcctgggg    840
caggaattat gcttccatca ttcgccgtga ctgcatgtgg agcggcttct ccgcccgaga    900
acggctggag agagtggtga cgacaggct ggccccaggc gcgccccggg ggaacccgcc     960
caaagcgccc gctaccccgg acggcactcc tagtctggaa gccagtaacc cggcgcccgc   1020
cacccaatgt cagctgggcg agcccaagac tcaggcctgc tccgggtccg agagcccag    1080
cgattctgaa ggtgaagaga ttgacgtggg accgtggag aagaggcgat ctctggacat    1140
ccgaaagcca gtcaccatca cggtgcgagc agacccctg gaccctgca tgaagcactt     1200
ccatatctct atccaccaac agcagcataa ctatgctgcc cgttttcctc agaaagttg    1260
ctctcaagag ggggatcctg agccaggtcc ccaggaagag gctccggaga tagaagctcc   1320
caaggagaaa gaggaggagg aagaggaaga ggaggaagaa gagattgtga gcccccacc    1380
tgtcggaagt gaggctcccc agtcctgcca ccccaaacct gtcagttctg cactgagga    1440
cgtgaccaag aggaagaacc ataacttctt ggaacgaaaa aggaggaatg acctccgctc   1500
ccggttccta gccctgcggg accaggttcc caccctggcc agctgctcta aggccccaa    1560
agtcgtgatc ctcagcaagg cgttagaata cttgcaggct ttggtggggg ctgaaaagaa   1620
aatggctaca gagaaaaggc agctccggtg tcggcaacag caactgcaaa agagaatcgc   1680
gtacctcagt ggctactaac cgaccagaac gcctgacttc ttggtctcac agacacaagc   1740
ttattgttta acctctctct cccttttagt aatttgcaca ttttggttac agcggggggg   1800
gcagtctgga cagtagatcc cagaatgcat tgcagccggt gtgcgcacac aataagggct   1860
tgcattcttg gtaacctcga aacccaattc tccctcttcc ccgaccgact catgggaatg   1920
ctgtccttct ctggcgcctt tggcttctca gcaggcagct actgaggaga tttggggtct   1980
gcttagctca ctagctcctg acgaaaggct gacagatgct atgcaacagg tggtggacgt   2040
tgttggggct gcagcctacg tgaaatctca cactgtgctg gggcttcagg ctaggaaagg   2100
atgctgctct cactgctgtc tctggggatg atctgaggac agctgggcct ggatactgtc   2160
ccccaggctc cgttttccag gaggcaagcg agctgtcccg ggcgaagaca agctcgcaga   2220
cttgatcagc atggagcatt acctcaccgt cagacacttt acagtagctg tggagtggaa   2280
acctttaaga tagatttgga tggtaggcca caccctccc tgcacgctca atgctatgac    2340
tttgagaaag ggcttggcct ctatgtagag tctttgtctc agagttctct gggcttctc    2400
agagagggac ctttctatcc tcacaaggga cctttttgtt tcttcctgcc tttgttatgc   2460
aatggccacc acagcaccct ttcacaccga ccagaaatat ttccccagga catagggaaa   2520
tgggtcacag cccaggacct ggggaagcct tggcatcccc actcatgacc aacggtcctt   2580
gcccaggttt tctgcagggc tatttgaggc ccagcttgga accttttctc gaggcagata   2640
gttacaaggt gcctctgaag gacaagccct atcgcttcct cttttccacc tgcctctctg   2700
tcagatcttg actctgtcta caatctgctg gaacagtgca aacctgtcct tctcgagcaa   2760
cttttgctggc tctgcagcca ccatcctgat tctctgccgg cctgagtcac atcctttccc   2820
```

-continued

```
ctggaatctg ggccttacag agagattcag aggggcaccg cttgcattca cctgatgccc      2880
ccagaaggta aacttacttc ctggtgggtt gtcagtgtac ctctaggaac gctactcagc      2940
caacaaggag agtttgctcc agctgtgttc tgcaactccc tgtggaatca agtacagcc      3000 ctctatcctg ggaaagtcac caagctagca gccgtcacgt gagcatcttt caggagatcc      3060
taagctttgc ctgaaagaag agccagcctt ccagaactc tacccaggaa agcagatctg      3120
ttcctgctgg ccctgggctt ggaagtaggg gtacagtgtg ggggacagac agtaagtaac      3180
aacatgtggc tctcaaaaac cagctaccac ttccaaattg ctcccaact gtgatggcct       3240 ccaattactt cctggcctca gtcctagag gaagcttcgg aagttgctgt tgtacctgtt       3300
ggggcaggac ttctaggcac caagggactc ctggaactat cttgggagga caagtggtga      3360
acaggctaaa gtctcatctg aatggcttgt gttttataag ctgctgcggg gttgtatgct      3420
gtgggcgtct tttgtttttg ttttgctttt ttttttaat actgtatttt tgtatgcttt       3480
tttgcaaagt ggtgttaact gttttgtat aagaaaaaca aaaacaaaa accctcctgt        3540 tgcaagggtc tggtttattt tgaaaggtgc atttacctga aattttgtat ttagttgtaa      3600
tcattaattg cttgatttta aactgttgcc ttctgggaca tcttctaata aaagatttc       3660 tcaaaaaaaa aaaaaaaaa aaaaaa                                            3686
```

<210> SEQ ID NO 9
<211> LENGTH: 3624
<212> TYPE: DNA
<213> ORGANISM: Homo sapiens

<400> SEQUENCE: 9

```
aatgcgcctg cagctcgcgc tcccgcgccg atcccgagag cgtccgggcc gccgtgcgcg        60
agcgagggag ggcgcgcgcg cggggggggc gcgcttgtga gtgcgggccg cgctctcggc       120
ggcgcgcatg tgcgtgtgtg ctggctgccg ggctgccccg agccggcggg gagccggtcc       180
gctccaggtg gcgggcggct ggagcgaggt gaggctgcgg gtggccaggg cacgggcgcg       240
ggtcccgcgg tgcgggctgg ctgcaggctg ccttctgggc acggcgcgcc ccgcccggc        300 cccgccgggc cctgggagct cgctccgggg cggcgctggc aaagtttgct ttgaactcgc       360
tgcccacagt cgggtccgcg cgctgcgatt ggcttcccct accactctga cccggggccc       420
ggcttcccgg gacgcgagga ctgggcgcag gctgcaagct ggtggggttg gggaggaacg       480
agagcccggc agccgactgt gccgagggac ccggggacac ctccttcgcc cggccggcac      540
ccggtcagca cgtcccccct tccctcccgc agggagcgga catggactac gactcgtacc      600
agcactattt ctacgactat gactgcgggg aggatttcta ccgctccacg gcgcccagcg      660
aggacatctg gaagaaattc gagctggtgc catcgccccc cacgtcgccg ccctgggggct      720 gggtcccgg cgcaggggac ccggccccg ggattggtcc cccggagccg tggcccggag         780
ggtgcaccgg agacgaagcg gaatcccggg gccactcgaa aggctgggc aggaactacg        840 cctccatcat acgccgtgac tgcatgtgga gcggcttctc ggcccgggaa cggctggaga      900
gagctgtgag cgaccggctc gctcctggcc cgccccgggg gaacccgccc aaggcgtccg      960
ccgccccgga ctgcactccc agcctcgaag ccggcaaccc ggcgcccgcc gcccctgtc      1020 cgctgggcga acccaagacc caggcctgct ccgggtccga gagcccaagc gactcggaga    1080
atgaagaaat tgatgttgtg acagtagaga agaggcagtc tctgggtatt cggaagccgg    1140
tcaccatcac ggtgcgagca gaccccctgg atcctgcat gaagcatttc cacatctcca    1200
```

-continued

```
tccatcagca acagcacaac tatgctgccc gttttcctcc agaaagctgc tcccaagaag    1260
aggcttcaga gaggggtccc caagaagagg ttctggagag atgctgca ggggaaaagg      1320
aagatgagga ggatgaagag attgtgagtc ccccacctgt agaaagtgag gctgcccagt    1380
cctgccaccc caaacctgtc agttctgata ctgaggatgt gaccaagagg aagaatcaca    1440
acttcctgga gcgcaagagg cggaatgacc tgcgttcgcg attcttggcg ctgagggacc    1500
aggtgcccac cctggccagc tgctccaagg cccccaaagt agtgatccta agcaaggcct    1560
tggaatactt gcaagccctg gtgggggctg agaagaggat ggctacagag aaaagacagc    1620
tccgatgccg gcagcagcag ttgcagaaaa gaattgcata cctcactggc tactaactga    1680
ccaaaaagcc tgacagttct gtcttacgaa gacacaagtt tatttttttaa cctccctctc   1740
cccttttagta atttgcacat tttggttatg gtgggacagt ctggacagta gatcccagaa   1800
tgcattgcag ccggtgcaca cacaataaag gcttgcattc ttgaaaccct tgaaacccag    1860
ctctcccctct tccctgactc atgggagtgc tgtatgttct ctggcgcctt tggcttccca   1920
gcaggcagct gactgaggag ccttggggtc tgcctagctc actagctctg aagaaaaggc    1980
tgacagatgc tatgcaacag gtggtggatg ttgtcagggg ctccagcctg catgaaatct    2040
cacactctgc atgagcttta ggctaggaaa ggatgctccc aactggtgtc tctggggtga    2100
tgcaaggaca gctgggcctg gatgctctcc ctgaggctcc ttttttccaga agacacacga   2160
gctgtcttgg gtgaagacaa gcttgcagac ttgatcaaca ttgaccatta cctcactgtc    2220
agacacttta cagtagccaa ggagttggaa acctttatat attatgatgt tagctgaccc    2280
ccttcctccc actcccaatg ctgcgaccct gggaacactt aaaaagcttg gcctctagat    2340
tctttgtctc agagccctct gggctctctc ctctgaggga gggacctttc tttcctcaca    2400
agggactttt ttgttccatt atgccttgtt atgcaatggg ctctacagca ccctttccca   2460
caggtcagaa atatttcccc aagacacagg gaaatcggtc ctagcctggg gcctggggat    2520
agcttggagt cctggcccat gaacttgatc cctgcccagg tgttttccga ggggcacttg    2580
aggcccagtc ttttctcaag gcaggtgtaa gacacctcag agggagaact gtactgctgc    2640
ctcttttccca cctgcctcat ctcaatcctt gagcggcaag tttgaagttc ttctggaacc   2700
atgcaaatct gtcctcctca tgcaattcca aggagcttgc tggctctgca gccaccccttg   2760
ggcccccttcc agcctgccat gaatcagata tcttttcccag aatctgggcg tttctgaagt  2820
tttggggaga gctgttggga ctcatccagt gctccagaag gtggacttgc ttctggtggg    2880
ttttaaagga gcctccagga gatatgctta gccaaccatg atggatttta ccccagctgg    2940
actcggcagc tccaagtgga atccacgtgc agcttctagt ctgggaaagt cacccaacct    3000
agcagttgtc atgtgggtaa cctcaggcac ctctaagcct gtcctggaag aaggaccagc    3060
agcccctcca gaactctgcc caggacagca ggtgcctgct ggctctgggt ttggaagttg    3120
gggtgggtag ggggtggtaa gtactatata tggctctgga aaaccagctg ctacttccaa    3180
atctattgtc cataatggtt tctttctgag gttgcttctt ggcctcagag accccaggg    3240
gatgtttgga aatagcctct ctacccttct ggagcatggt ttacaaaagc cagctgactt    3300
ctggaattgt ctatgcagga cagtttgggt gtaggttact gatgtctcaa ctgaatagct    3360
tgtgttttat aagctgctgt tggctattat gctgggggag tcttttttttt ttatattgta  3420
tttttgtatg ccttttgcaa agtggtgtta actgttttttg tacaaggaaa aaaactcttg   3480
gggcaatttc ctgttgcaag ggtctgattt atttttgaaag gcaagttcac ctgaaatttt   3540
gtatttagtt gtgattactg attgcctgat tttaaaatgt tgccttctgg gacatcttct    3600
```
aataaaagat ttctcaaaca tgtc                                                3624

<210> SEQ ID NO 10
<211> LENGTH: 3480
<212> TYPE: DNA
<213> ORGANISM: Mus musculus

<400> SEQUENCE: 10

| | | | | | |
|---|---|---|---|---|---|
| cctttgcctc | cggacttctc | tggggccagc | agccgcccga | cctggggccc | ggggccacgg | 60 |
| gctcagcaga | cgaccatggg | ctcggtgtcc | aaccagcagt | tgcaggtgg | ctgcgccaag | 120 |
| gcagcggaga | aggcgccaga | ggaggcgccg | cctgacgcgg | cccgagcggc | agacgagccg | 180 |
| cagctgctgc | acgggccgg | catctgtaag | tggttcaacg | tgcgcatggg | gttcggcttc | 240 |
| ctgtctatga | ccgcccgcgc | tggggtcgcg | ctcgaccccc | cggtggacgt | ctttgtgcac | 300 |
| cagagcaagc | tgcacatgga | agggttccga | agcctcaagg | agggtgaggc | ggtggagttc | 360 |
| acctttaaga | agtctgccaa | gggtctggaa | tccatccgtg | tcactggccc | tggtggtgtg | 420 |
| ttctgtattg | ggagtgagcg | gcggccaaaa | gggaagaaca | tgcagaagcg | aagatccaaa | 480 |
| ggagacaggt | gctacaactg | cggtgggcta | gaccatcatg | ccaaggaatg | caagctgcca | 540 |
| ccccagccca | agaagtgcca | cttttgccaa | agcatcaacc | atatggtggc | ctcgtgtcca | 600 |
| ctgaaggccc | agcagggccc | cagttctcag | ggaaagcctg | cctacttccg | ggaggaagag | 660 |
| gaagagatcc | acagccctgc | cctgctccca | gaagcccaga | attgaggccc | aggagtcagg | 720 |
| gttattcttt | ggctaatggg | gagtttaagg | aaagaggcat | caatctgcag | agtggagaaa | 780 |
| gtggggtaa | gggtgggttg | cgtgggtagc | ttgcactgcc | gtgtctcagg | ccggggttcc | 840 |
| cagtgtcacc | ctgtctttcc | ttggagggaa | ggaaaggatg | agacaaagga | actcctacca | 900 |
| cactctatct | gaaagcaagt | gaaggctttt | gtggggagga | accaccctag | aacccgaggc | 960 |
| tttgccaagt | ggctgggcta | gggaagttct | tttgtagaag | gctgtgtgat | atttcccttg | 1020 |
| ccagacggga | agcgaaacaa | gtgtcaaacc | aagattactg | aacctacccc | tccagctact | 1080 |
| atgttctggg | gaagggactc | ccaggagcag | ggcgaggtta | ttttcacacc | gtgcttattc | 1140 |
| ataaccctgt | cctttggtgc | tgtgctggga | atggtctcta | gcaacgggtt | gtgatgacag | 1200 |
| gcaaagaggg | tggttgggga | gacaactgct | gacctgctgc | ccacacctca | ctcccagccc | 1260 |
| tttctgggcc | aatgggattt | taatttattt | gctcccttag | gtaactgcac | cttgggtccc | 1320 |
| actttctcca | ggatgccaac | tgcactatct | acgtgcgaat | gacgtatctt | gtgcgttttt | 1380 |
| ttttttttta | attttaaaa | ttttttttca | tcttcttaat | ataaataatg | ggtttgtatt | 1440 |
| tttgtatatt | ttaatcttaa | ggccctcatt | cctgcactgt | gttctcaggt | acatgagcaa | 1500 |
| tctcagggat | aataagtccg | tagcagctcc | aggtctgctc | agcaggaata | ctttgttttg | 1560 |
| ttttgttttg | atcaccatgg | agaccaacca | tttggagtgc | acagcctgtt | gaactacctc | 1620 |
| attttgccg | attacagctg | gcttttctgc | catagcgtcc | ttgaaaaatg | tgtctcacgg | 1680 |
| gtttcgattg | agctgcccca | agacttgatc | tggatttggc | aaaacatagg | acatcactct | 1740 |
| aaacaggaaa | gggtggtaca | gagacattaa | aaggctgggc | caggtgaaag | gcacaagagg | 1800 |
| aactttccat | accagatcca | tccttttgcc | agattagtgg | aagcctgcca | tgcacagcag | 1860 |
| ggtgtgagag | agagagtgtg | tatgtatgtg | tgtgtggatt | ttttttaatg | caaatttatg | 1920 |
| aagacgaggt | gggttttgtt | tatttgattg | cttttgtgc | tggggatgga | atctgggct | 1980 |
| tcatttgtgc | taggaagtac | actgccactg | agttatccca | gtaagaatgc | aacttaagac | 2040 |

| | |
|---|---|
| cagtacccتt attcccacac tgtgctgtcc aggcatggga acatgaggca gggactcaac | 2100 |
| tccttagcct ttcacaatct tggctttctg agagactcat gagtatgggc ctcagtggca | 2160 |
| agtgtcctgc cctgctgtag cgtgatggtt gatagctaaa ggaagaggg ggtgggggt | 2220 |
| ttcgtttaca tgctttgaga tcgccacaaa cctacctcac tgtgttgaaa cgggacaaat | 2280 |
| gcaatagaac acattgggtg gtgtgtgtgt gtgtctgatc ttggtttctt gtctccctct | 2340 |
| cccccaaat gctgccctca cccctagtta attgtattcg tctggccttt gtaggacttt | 2400 |
| tactgtctct gagttggtga ttgctaggtg gcctagttgt gtaaatataa atgtgttggt | 2460 |
| cttcatgttc ttttgggtt ttattgttta caaaacttt gttgtattga gagaaaata | 2520 |
| gccaaagcat ctttgacaga aagctctgca ccagacaaca ccatctgaaa cttaaatgtg | 2580 |
| cggtcctctt ctcaaagtga acctctggga ccatggctta ccttacctg ttcctcctgt | 2640 |
| gtctcccatt ctggaccaca gtgaccttca gacagcccct cttctccctc gtaagaaaac | 2700 |
| ttaggctcat ttacttcttt gagcatctct gtaactcttg aaggacccat gtgaaaattc | 2760 |
| tgaagaagcc aggaacctca ttcttcctt gtccctaact cagtgaagag ttttggttgg | 2820 |
| tggttttgag acagggcctc actctgtagc tggagataga gagcctcggg ttcctggctc | 2880 |
| tcctcctgcc ttctgcacag agtcccctgt gcagggattg caggtgccgc ttctccctgg | 2940 |
| caagaccatt tatttcatgg tgtgattcgc ctttggatgg atcaaaccaa tgtaatctgt | 3000 |
| cacccttagg tcgagagaag caattgtggg gccttccatg tagaaagttg gaatctggac | 3060 |
| accagaaaag ggactatgaa tgtacagtga gtcactcagg aacttaatgc cggtgcaaga | 3120 |
| aacttatgtc aaagaggcca caagattgtt actaggagac ggacgaatgt atctccatgt | 3180 |
| ttactgctag aaaccaaagc tttgtgagaa atcttgaatt tatggggagg gtgggaaggg | 3240 |
| gtgtacttgt ctgtcctttc cccatctctt tcctgaactg caggagacta aggcccccca | 3300 |
| cccccgggg cttggatgac ccccaccccct gcctgggtg ttttatttcc tagttgattt | 3360 |
| ttactgtacc cgggccttg tattcctatc gtataatcat cctgtgacac atgctgactt | 3420 |
| ttccttccct tctcttccct gggaaaataa agacttattg gtactccaga gttggtactg | 3480 |

<210> SEQ ID NO 11
<211> LENGTH: 4024
<212> TYPE: DNA
<213> ORGANISM: Homo sapiens

<400> SEQUENCE: 11

| | |
|---|---|
| caccgctatt gtgcggggga agatgtagca gcttcttctc cgaaccaacc ctttgccttc | 60 |
| ggacttctcc ggggccagca gccgcccgac caggggcccg gggccacggg ctcagccgac | 120 |
| gaccatgggc tccgtgtcca accagcagtt tgcaggtggc tgcgccaagg cggcagaaga | 180 |
| ggcgcccgag gaggcgccgg aggacgcggc ccggcggcg gacgagcctc agctgctgca | 240 |
| cggtgcgggc atctgtaagt ggttcaacgt gcgcatgggg ttcggcttcc tgtccatgac | 300 |
| cgccccgcgcc ggggtcgcgc tcgacccccc agtggatgtc tttgtgcacc agagtaagct | 360 |
| gcacatggaa gggttccgga gcttgaagga gggtgaggca gtggagttca cctttaagaa | 420 |
| gtcagccaag ggtctggaat ccatccgtgt caccggacct ggtggagtat tctgtattgg | 480 |
| gagtgagagg cggccaaaag gaaagagcat gcagaagcgc agatcaaaag gagacaggtg | 540 |
| ctacaactgt ggaggtctag atcatcatgc caaggaatgc aagctgccac cccagcccaa | 600 |
| gaagtgccac ttctgccaga gcatcagcca tgtagcc tcatgtccgc tgaaggccca | 660 |
| gcagggccct agtgcacagg gaaagccaac ctactttcga gaggaagaag aagaaatcca | 720 |

-continued

```
cagccctacc ctgctcccgg aggcacagaa ttgagccaca atgggtgggg gctattcttt      780
tgctatcagg aagttttgag gagcaggcag agtggagaaa gtgggaatag ggtgcattgg      840
ggctagttgg cactgccatg tatctcaggc ttgggttcac accatcaccc tttcttccct      900
ctaggtgggg ggaaagggtg agtcaaagga actccaacca tgctctgtcc aaatgcaagt      960
gagggttctg ggggcaacca ggagggggga atcaccctac aacctgcata ctttgagtct     1020
ccatccccag aatttccagc ttttgaaagt ggcctggata gggaagttgt tttccttta      1080 aagaaggata tataataatt cccatgccag agtgaaatga ttaagtataa gaccagattc     1140
atggagccaa gccactacat tctgtggaag gagatctctc aggagtaagc attgtttttt     1200
tttcacatct tgtatcctca tacccacttt tgggataggg tgctggcagc tgtcccaagc     1260
aatgggtaat gatgatggca aaagggtgt ttgggggaac agctgcagac ctgctgctct      1320
atgctcaccc ccgcccatt ctgggccaat gtgatttat ttatttgctc ccttggatac       1380
tgcaccttgg gtcccacttt ctccaggatg ccaactgcac tagctgtgtg cgaatgacgt     1440
atcttgtgca ttttaacttt ttttccttaa tataaatatt ctggttttgt attttgtat     1500 attttaatct aaggccctca tttcctgcac tgtgttctca ggtacatgag caatctcagg     1560
gatagccagc agcagctcca ggtctgcgca gcaggaatta cttttgttg tttttgccac      1620 cgtggagagc aactatttgg agtgcacagc ctattgaact acctcatttt tgccaataag     1680
agctggcttt tctgccatag tgtcctcttg aaaccccctc tgccttgaaa atgttttatg     1740
ggagactagg ttttaactgg gtggccccat gacttgattg ccttctactg gaagattggg     1800
aattagtcta aacaggaaat ggtggtacac agaggctagg agaggctggg cccggtgaaa     1860
aggccagaga gcaagccaag attaggtgag ggttgtctaa tcctatggca caggacgtgc     1920
tttacatctc cagatctgtt cttcaccaga ttaggttagg cctaccatgt gccacagggt     1980
gtgtgtgtgt ttgtaaaact agagttgcta aggataagtt taaagaccaa taccctgta     2040 cttaatcctg tgctgtcgag ggatggatat atgaagtaag gtgagatcct taaccttca      2100 aaatttcgg gttccaggga gacacacaag cgagggtttt gtggtgcctg gagcctgtgt      2160
cctgccctgc tacagtagtg attaatagtg tcatggtagc taaaggagaa aagggggtt      2220 tcgtttacac gctgtgagat caccgcaaac ctaccttact gtgttgaaac gggacaaatg     2280
caatagaacg cattgggtgg tgtgtgtctg atcctgggtt cttgtctccc ctaaatgctg     2340 cccccaagt tactgtattt gtctgggctt tgtaggactt cactacgttg attgctaggt      2400
ggcctagttt gtgtaaatat aatgtattgg tcttctccg tgttctttgg gggttttgtt      2460
tacaaacttc ttttttgtatt gagagaaaaa tagccaaagc atctttgaca gaaggttctg     2520
caccaggcaa aaagatctga aacattagtt tggggggccc tcttcttaaa gtggggatct     2580
tgaaccatcc tttcttttgt attcccttc ccctattacc tattagacca gatcttctgt       2640
cctaaaaact tgtcttctac cctgccctct tttctgttca ccccccaaaag aaaacttaca     2700 cacccacaca catacacatt tcatgcttgg agtgtctcca caactcttaa atgatgtatg     2760
caaaaatact gaagctagga aaaccctcca tcccttgttc ccaacctcct aagtcaagac     2820
cattaccatt tctttctttc tttttttttt tttttaaaa tggagtctca ctgtgtcacc      2880
caggctggag tgcagtggca tgatcggctc actgcagcct ctgccttcttg ggttcaagtg     2940 attctcctgc ctcagcctcc tgagtagctg ggatttcagg caccagccac actcagctaa     3000
tttttgtatt tttagtagag acggggtttc accatgttgt ccaggctggt ctggaactcc     3060
```

```
tgacctcagg tgatctgccc accttggctt cccaaagtgc tgggattaca ggcatgagcc    3120
accatgctgg gccaaccatt tcttggtgta ttcatgccaa acacttaaga cactgctgta    3180
gcccaggcgc ggtggctcac acctgtaatc ccagcacttt ggaaggctga ggcgggcgga    3240
tcacaaggtc acgagttcaa aactatcctg gccaacacag tgaaacccg tctctactaa    3300 aatacaaaaa aattagccgg gtgtggtggt gcatgccttt agtcctagct attcaggagg    3360
ctgaggcagg ggaatcgctt gaacccgaga ggcagaggtt gcagtgagct gagatcgcac    3420
cactgcactc cagcctggtt acagagcaag actctgtctc aaacaaaaca aacaaaaca    3480 aaaacacact actgtatttt ggatggatca aacctcctta atttaatttt ctaatcctaa    3540
agtaaagaga tgcaattggg ggccttccat gtagaaagtg gggtcaggag gccaagaaag    3600
ggaatatgaa tgtatatcca agtcactcag gaacttttat gcaggtgcta gaaactttat    3660
gtcaaagtgg ccacaagatt gtttaatagg agacgaacga atgtaactcc atgtttactg    3720
ctaaaaccca agctttgtg taaaatcttg aatttatggg gcgggagggt aggaaagcct    3780
gtacctgtct gtttttttcc tgatcctttt ccctcattcc tgaactgcag gagactgagc    3840
ccctttgggc tttggtgacc ccatcactgg ggtgtgttta tttgatggtt gattttgctg    3900
tactgggtac ttcctttccc attttctaat cattttttaa cacaagctga ctcttccctt    3960
cccttctcct ttccctggga aaatacaatg aataaataaa gacttattgg tacgcaaact    4020
gtca                                                                4024

<210> SEQ ID NO 12
<211> LENGTH: 5420
<212> TYPE: DNA
<213> ORGANISM: Mus musculus

<400> SEQUENCE: 12
aagaaggaaa gcacattaga ccatgcgaac taaatttgtg atcgcacaaa atcaagatgt      60
tagactgatg ctgaagatca ctccggtcca aagggaaagt tttcatctct ggagtttgaa     120
gctgagggcc ggtggggcaa catggccgaa ggcggggcaa gcaaggtga agagccagaa     180 aaactgcccg gctggcaga ggacgaaccc caggttctgc atggcactgg ccactgtaaa     240
tggttcaacg tgcgcatggg attcggattc atctccatga taagtcgaga gggaaatccc     300
ttggatattc cagtggatgt atttgtacac caaagcaaac tattcatgga aggatttaga     360
agcttgaaag aaggagagcc agtggaattt acatttaaaa atcccccaa aggccttgag     420 tcaatacggg taacaggccc agtgggagc ccctgcttag gaagtgaaag aagacctaaa     480
ggaagacccc tgcaaaagag aaagccaaag ggagataggt ggagacggca ggatttactg     540
atggatcaga tgtggactgt gcgagaagaa gagtccagga tgattccaag atgctacaac     600
tgtggtggtc tcgaccatca tgctaaagaa tgcagtctac ctcctcagcc aaagaagtgc     660
cattactgtc agagcatcat gcacatggtg gccaactgcc cacacaagct tgccgctcag     720
ctgcccgcca gttctcaggg aagacaggag gcagaatccc agccatgcag ctctgcggca     780
ccaagagaag tgggaggggg gcatggctgc acagtactgt ttcctcagga ggtgaagtca     840
gaaatggcag agcactcaga caggtcaccc caagaagttt cttccacgaa agcgtttgca     900
gcaataggag agcaaaacaa aaaggggcct tgattcaga aacggaaaaa gacttagtac     960
ttgtcagtgt tcccttcacc cgggcgggaa gtctacctca tgcaagcaca ggggaatagt    1020
ggtccacaga gagcagccgg ccgggatgtt aactactgct gaggaactgg gaagttctta    1080
attagacaaa tcactcttaa gcaaactaca tttaagcagg gtgtcatgtt ttatagaatt    1140
```

```
gagatactac atatagtatg tgcataagtg agagggggaga cttgaatctg tatgtatgtg    1200
tgaggatttc acataagagt acaggcacac acacacatat atatatacac ttttatatat    1260
ctgtggttgt cttttgtgtgt gtgtgtgtgt gtatgtgtgt gtgtgtgtgt gtgtatgtag   1320
ataaaagcac atactcttcc tcagataatt gggcatctct aagcattgaa aatccatgtg    1380
aagcatttga gatggtttca tagttaaccc ttggaatttt ttctaaatac tacttctttt    1440
atattatgta aaaaatgacc acgtgactgt tacctttcat gtgaaccaaa gcatacttca    1500
gatctcagag ctgccagtca aatggtacta aaggcttttg ggatacttgg tgcctcccaa    1560
gtctgtattc ataactctat cttgatgctg atagagtgtt ttgctgttgc tgttatctgt    1620
cttctcctgt ttgaaggtag taacttaact ctagatgcct ccgactgcca taagctttta    1680
atccttggat acgtagctcc agaaaagaca atgaatgtga acttcctgtg ctgatatttc    1740
agtgtctttt attctgtttg attgtaaatt acatggctat taagaaaaat gaaggggagg    1800
gtaatgtata tagtaacatg gtcccttttca gtggtatttt gatgctaggt cttttacaag   1860
ggttctgagg ttttttaaggg atggtggcaa cagaagcctc ctttgactaa gtagcttttg   1920
aaccatcact tagatcagga aggtctctta cttactactg aagccttaga gaaaatttta   1980
attatttggg tatattttg gtagctgttt ttatttcccc tggagagtcc tcagacctgt     2040
ttataaaaca aacaaaagca gcatagaaat aaaatagtgg ggcttagaat gaaaattaag   2100
ttgcccaata gatacagccc atgattgata ctaaaaagaa tagtgtttga tggccagcag    2160
agtgaatgag tggagcagag ttaccaaagt gcccactgtt ctgtggctag aaatacttta   2220
tatgataata ttgatgccat ggcaggttcc ttgagtatag aagcggaagt atggtgtgtg   2280
atagattcag gatgagcact cagatcaagt tataggatct tctcagatgg attctcagtt   2340
tgctaagatt ggctaggaac tgattgtagt attgggctgt tttccatcat gttttgtttt    2400
cttttgtttt ttgaatggag ttagcctggt tctaaatgtc atgagcaaac ttttgaaaca   2460
tcttcaagaa ggtaccaagg gattgcagtg cataattttg gctgtaacta tatgggcctg   2520
ttggtataag ctcagataat caaacaagaa agcatcgtga ctcatgagac acattctacg    2580
gaggagtcgc ttcctcctgt gtgtcttgtc atgggagttg ggtggtgcta aggtttcatc    2640
aagccactag aagaagaaag tgtctccgac tagcttacca gtcttttcca gagtagcttg    2700
aattgcttga cagtatttat gagagttcct atagtgtttt accgaagtgt cagtgtgctg    2760
taatacagag cttacctttg acgatattga atgtgatgta gccatagaga agtgctgcct   2820
tgccttacgt gaggatttca agcttattta aattatgtag acaaatcaaa ggtcatccaa   2880
gtataatgag caaggtaaca gttgtacaag caaaatatga taggtcactc tgaacgctca    2940
aaccaaagtt ccttgactat caaaatagga aataatggac ttgaaaactg gacattctgt    3000
ttacatttaa aatttaagag ctgaggtcat tttaacaaat gaaagtagaa aattcagaaa    3060
cacttgaata tagaccttat gggtgcagtc aacttctttt cagcatctaa ccagaccgac   3120
ttactaaaag cacataccaa acctatctta tggttaaaag tttatttttt atatgaaaat    3180
agtgtcacta ttcatgctc aggacaaaga actttgctca gggaacatac catataatgt     3240
ttttattgtt tttttttgtt ttgttttgtt ttgttttgtt ttttacaga ctaatgtata     3300 atcctgcttt ctcagagcaa gccaaataaa ttaagtcttt atgtacgtac atatacttgt    3360
tagtaactac ctctgagttt gacattgatc ataattctga atatcagata ttggtcctcc    3420 cttttttaaat ttcatgtcaa agtcttgtaa agcggaattc cactacctgc agatgtgaac   3480
```

| | |
|---|---|
| tcactgatat gagcacttgc tcattcacac aagtgaaaat tctgtttaca gcacatggct | 3540 |
| acctcccagc taccacagag cacaccttga tgctgctgca gcctgcaggt tgctgataat | 3600 |
| tctctggtac agacgctttt aatctgtagc acagataggc atttgcaact gcatgtttct | 3660 |
| gaaaaacgcc tgttttttctc atagatttct catgttaagt agcaaaatct ccaagcattt | 3720 |
| ccttagagtt atcatgtatt aaatgtaagg aagtatggac actctaattt atcctaggcc | 3780 |
| aaacagaaca cagaaacaat cttgaaaata gctctgttac ctagaggtga ggggcagcag | 3840 |
| agataacaaa aggaaacttg gtgtttgtat tttgctgaca agtgttataa aagattccta | 3900 |
| ccgcttcact tgtatctcta cagtactgaa ggcaaagcat actgcagcat tccaagcctc | 3960 |
| aggcacacaa ctaactagca ccagcttgcc atggggaaac ttaaagtgca gtgttgcctt | 4020 |
| gagccagagg ggaacggggt ctgtggagca ccactttgca ggggttcctc atagtgcggt | 4080 |
| gtggtttgag ccatcttttg acctcccccct tacagcaaca caaatgtaac tcctaaaaaa | 4140 |
| cgattcacta ccagccttta gcctgcgaac tattcgttct ctacacagca ggacacagtg | 4200 |
| gacacatttt tatacttgca tttctaatct ttggatgtat ttttacaaat gaaagactta | 4260 |
| ggaagatttt tatctgctta tcacctggaa attttagtgt gcaatctaaa gaaaagata | 4320 |
| aagacatcac attattagca tcagtccacc tcccaaatat aggatgtttt attgccaatt | 4380 |
| attttgtat tctggctgag ctttattttg caccagggca ggcctaactt gccgctggtt | 4440 |
| gtatgtagtt tgtgaataga agcccataag tgttaataga ccttgtaaca ttcgctgtaa | 4500 |
| gatgaattat acaggatgtg gggaatctca gtaagtctta aagttaattt aaagtaattt | 4560 |
| atctgttttc tctaagaaat gtttatcata aaatatatat gtaacttccc attttggtat | 4620 |
| aaaatctagg gaagtgtgtg caagtggagt tgtgctgact ttgaatttct agatgtctta | 4680 |
| atgagattta tttgttttag aaaaagaaca acttgttgaa agcacccagt tctgtcttac | 4740 |
| atactgtcaa cagcctcttc aagttgtgcc tgtgtgatct gtgacctcct gttcctttaa | 4800 |
| agtgagacag tgacctatga ctcattgttg accttatact tggaacagaa ctacggcatt | 4860 |
| tacggtggag tcctgtacga cgagaaagtg tcaggatatg caacgcacct gtggcttacc | 4920 |
| ccttgacggc ccagcttgga aatgatggca ccgactacct cttcaatcac ttgtggctat | 4980 |
| caaccacagg cacttagcac caggctggct ttaattagtg tgtgttgttt ttgtggtggt | 5040 |
| aacaactcta tccatatgaa gaccaaagtg aaccctggtt tctatatgtc tttaatgcag | 5100 |
| tgttgtatct agtatttgga aattatctca ttcagtgttt agattacctc actccatttt | 5160 |
| gattcatgtt gtttacaagt gaacattttt ttaaagatac acttgaaatt gcgttagaaa | 5220 |
| gaacaaagga ggagttgcta ttagactggc acagtgcatt ccacagactt ggtggactgc | 5280 |
| tctctgcaga catgggccta ggactgtctt tgtaccgaat gtcttactct gttggctatt | 5340 |
| gatgtttaaa atttcatgat agaaaataaa agacacaatg ttggtgttta agatgggttt | 5400 |
| ggaaaaaaaa aaaaaaaaa | 5420 |

<210> SEQ ID NO 13
<211> LENGTH: 5517
<212> TYPE: DNA
<213> ORGANISM: Homo sapiens

<400> SEQUENCE: 13

| | |
|---|---|
| aattgacaaa gtcacgtgtg ctcagggggc cagaaactgg agagaggaga gaaaaaaatc | 60 |
| aaaagaagga aagcacatta gaccatgcga gctaaatttg tgatcgcaca aaatcaagat | 120 |
| gttagattga tgcagaagat cactccgttc caaagggaaa gttttcatct cacgagtttg | 180 |

```
gagctgaggg cccgtggggc aacatggccg aaggcggggc tagcaaaggt ggtggagaag    240
agcccgggaa gctgccggag ccggcagagg aggaatccca ggttttgcgc ggaactggcc    300
actgtaagtg gttcaatgtg cgcatgggat ttggattcat ctccatgata aaccgagagg    360 gaagccccett ggatattcca gtcgatgtat ttgtacacca aagcaaacta ttcatggaag    420
gatttagaag cctaaaagaa ggagaaccag tggaattcac atttaaaaaa tcttccaaag    480
gccttgagtc aatacgggta acaggacctg gtgggagccc ctgtttagga agtgaaagaa    540
gacccaaagg gaagacacta cagaaaagaa aaccaaaggg agatagatgc tacaactgtg    600
gtggccttga tcatcatgct aaggaatgta gtctacctcc tcagccaaag aagtgccatt    660
actgtcagag catcatgcac atggtggcaa actgcccaca taaaaatgtt gcacagccac    720
ccgcgagttc tcagggaaga caggaagcag aatcccagcc atgcacttca actctccctc    780
gagaagtggg aggcgggcat ggctgtacat caccaccgtt tcctcaggag gctagggcag    840
agatctcaga acggtcaggc aggtcacctc aagaagcttc ctccacgaag tcatctatag    900
caccagaaga gcaaagcaaa aaggggcctt cagttcaaaa aaggaaaaag ataacagg     960 tcttcttcat atgttctttc ctttacccgg ttgcaaagtc tacctcatgc aagtataggg   1020
gaacagtatt tcacaagcag tagctgacct gggatttaa ctactattgg ggaactgtga    1080
attttttaaa cagacaaatc actctaagca aattacattt gagcagggtg tcatgtttta   1140
tgttaattca gagaataaga tactatgtct gtcaatatgt gcatgtgtga gagggagaga   1200
gcctgagtct gtgtgtgtac atgaggattt ttatatagga atgtagacac atatataaag   1260
aggctttgtc tttatatatt tgtgtataga tcaaagcaca caccctctct catataattg   1320
gatatttcca agaattgaaa acccatgtga agcattatag atagttttaa atttaaccca   1380
ctggagtttt cttgaaatac cacttctttt atattatata aaactaaaaa cacgactgtt   1440
accttttgtg tgaaccaaag gatacttcag atctcagagc tgccaattat ggggtactaa   1500 aggttttta gacatccagt tctcccgaat ttgggattgc ctcttttct tgaaatctct     1560 ggagtagtaa tttttttccc ccttttttga aggcagtacc ttaacttcat atgcctctga   1620
ctgccataag ctttttgat tctgggataa cataactcca gaaaagacaa tgaatgtgta    1680
atttgggccg atatttcact gttttaaatt ctgtgtttaa ttgtaaaatt agatgcctat   1740
taagagaaat gaaggggagg atcatcttag tggcttgttt tcagtagtat tttaatatca   1800
gcttcttgta acctttttcca tgttgtgagg gttgtaaggg attgtgtggc aacagcagct   1860
tcccttggct aactcaatct tctacccatt gcttagagca gggagccctc cttatttact   1920
actgaagacc ttagagaact ccaattgttt ggcatatatt tttggtggtg gttttattc    1980 ctcctggaga gttatctaat ttgtttctaa aacaaacaag cagcaaagaa atgaattaaa   2040
tactggggtt gagaattaaa attaagtgga tgttcacagt tgcccaatat atatgacctg   2100
caaatgatac gaaaaagtgc agcatttagt ggcagttaac aagagtgaca agcctgggc    2160 agaggtacca aacctctccc accagagagc tagaagtatt ttatacagta actttgatct   2220
tatggaagtg accttcaatg cttattctga agtaacctat atggtggata caggatgaac   2280
attcagtgcc agggagaatc ttctcaggtt ggttctcgtt agagtgataa actggctagg   2340
ggccatagta ttggtcctgt taggtttcgg tcatggaaaa aaaaattatt ttgggggtcat   2400 cctggctcta gatgttatgg gcaaatttct gaaacatctg caagaaggta ccagttaatt   2460
atagtgctta atattgggaa taagattaag cattataatt ataatgtatg ggcctgttgg   2520
```

```
tgtaagctca gataattaaa taaaaatagc atgactcaaa tgagacatat tctgctgaac   2580
agtttctact tcctctcccg cctgtcctgt catgggagac gtgtatagtt gctgctgttt   2640
cagcaaacca ccataagacg aaaatgcctc aggttgggtt gccagtcctt tacaactcag   2700
cttgaatttc acaacagtga ttgtgagaat ctgcgtggta tacactgaaa tatcggtgtg   2760
ctgtgatgca aagcttacct ttgacgatat tgaatgtgat atagctgtag agaagtactt   2820
ccttgcctta tgtgaggatt tcaaacttat ttaaattatg tagacaaatc aaagtggcat   2880
tgcttaattt ttagcaggca taataagcaa gttaacagta aaatgcaaaa catgataagc   2940
gttgctcaat ttttagcagg tataataagc aggttaacag taaaaatgca aaacatgata   3000
gataagtcac tttgaaaatt caaaccaaag ttccttcacc ttatggaaat aggaaattat   3060
ggacttcaaa attggacact tcctgtttac aaaaagaaat tcagagctaa aatcatggta   3120
aaaaaaaata gaaacacttg agaactatgg tctttatggg tgcaatttga aatccttttc   3180
atcatcttac cagactaaac taagagcaca taccaaacct atcttatggt tgaaagttgg   3240
ggtttatttt ttatatgaga atattatcac tattacataa catactcagg acaaagaact   3300
ttgctcaggg aacataccat gtaatatttt tgttgtttct ttacagacta gtctacagtc   3360
ctgcttactc aaaacaaacc aaataactta tcctttata taagtattat gtactgatga   3420
tagtaactac ctctgagttt gacacagatc aaaattttg aatatcagat atcagttatc   3480 ctattttat ttcatgtgaa aactcctcta aagcagattc cctcaactct gtgcatatgt    3540
gaatatcact gatgtgaaca cattgttcat ttacataggt aaaatattac tctgtttaca    3600
gcaaaaggct acctcatagt tgatacatag cacacctgta tgtatgctgt tccagcctta    3660
caggtggctg ataattctct ggtacagaac cttttatct gtattataaa tagcaattca    3720
caactgcatg tttctgacaa acacttgtga ataatgaagc atctcgtttt agttagcaaa    3780
gtctccaaac atttccttaa aataatcatg tatttagttt aaagaattat gggcactgtt    3840
caacttaagc aaaacagaac acggaagcag tcttagaagc accactttgc ccagaggtgg    3900
aggttggaag gggtagcagg gagagggggtt ggtgtatgca ggtattcatg ctaggcaaag    3960
agtttaaaag acgccaatgt ccttcattta ctgtctgtgc tgccctgaag ccaagcgtat    4020
tgcagcatta tagccccagg cacataacta actagcactg gcttgccaag gaatgaacat    4080
gcaatgccat tactagctat tgagggaaaa gggtctgtgt gaagcatcac tttgcaggga    4140
ttactaatgg tggggcagca ggtctgtgaa ttaagttatc tcttgacctc accctcatgt    4200
caacacaaat gtaattccta acaagatgc attgccagtc tcttagccct gtaagctgat    4260
cttttgctac atggcagact ataatgaaaa catttttata cttgggtttc tagtcttcac    4320
tagaaggcct tggatgtatt tttgcagttg aaagatttag aaagattttt acctgcttat    4380
aacttggaag tttagagtgc aatgtaagaa aaaagatcaa gaaatgtcat gttattagca    4440
tcagtccacc tccaatattg ccgatacttt ttttattctg gctcagtttt attttgcacc    4500
agtgcggccc caagttactg ctggttgtat ttagtttgtg aataggagcc cataagtgtt    4560
aatagacttt gtaacattca ctataagatg aattatacag gacatgggaa atctcattaa    4620
gtcttaaagt taatttaaat taatttatct gttttctcta agaaatgttt atcataaaat    4680
atatatgtgt atttcccctt tggttataaa atttgggaaa gtatgtacaa gtgcagctgc    4740 actgactttta attttctaga tgtcttaatg agatttattt gttttagaga agaacatctt   4800
gttaaaagca tcaaactctg tcttacatag ctgtcaacag cctctttaag atgtggtggt    4860
tgtatgatct gtgtcttaat tgttcagtta gagtgagaag ttgacctatg attcattttt    4920
```

```
aaatttata tttggaacaa agctgcaagt tatggtaaag tactgtactg tgagaagtat    4980
tatgatattt aatgcatctg tggcttaaca cttgtgagag ttaccagctt gaaaatgatg    5040
gtgttgacta cctcttgaat cacatctatc aaccactggc acctaccacc aagctggctt    5100
caattagtat gtgttgcttt ttggtattaa caactaaccg tactagagac caaagtgaac    5160 cctgatttt atatgtcttt aataatggtg ttttatctag tgttttaaa ttatcctgtg    5220 tagtatttag attacctcat tgtccatttt gactcatgtt gtttacaagt gaaaataaaa    5280
acacttgaac tgtatgtttt taaaagacaa aaaggggta gatgtttgga atgcgtttca    5340
ctcgcatgca gtcatctgga gggactgaag cactgtttgc ctttctgtac actctgggtt    5400
ttatattctc atttcatgcc taatgtctta ttctgtcaat tatggatatg ttgaggttta    5460
aaaaaattac ttgattaaaa ataaaacata taacgttggc atttaaaaaa aaaaaaa      5517

<210> SEQ ID NO 14
<211> LENGTH: 4208
<212> TYPE: DNA
<213> ORGANISM: Mus musculus

<400> SEQUENCE: 14
agtgggctcc aagtgtcggg cgccccagcc tcctccacgg cttggcgtcc cctctgcccg      60
ttcgctgagc gcgcggatga gtgggagcgc ggagctgcgc gcggctctct gcctccggct     120
cccccgccgc ggccgcgtcc tcccactccg ccttctcgcg ctcaccgtgc ccgccggccg     180
ggactcgcac ctcgcctgtg cccttcactc gtcttccgcg tgatttgccc gccgcctttc     240
tcctccaact gggaatgcta aaacgggact gatggacgtg tccgaactct gcatcccgga     300
ccccctgggc taccacaacc agctgctgaa ccgaatgtcg tccgaagaca ggcacctggg     360
ctctagttgc ggctccttca tcaagacgga gccatccagc ccgtcctcgg gcattgatgc     420
cctcagccac cacagcccca gcggctcgtc ggacgccagt ggtggctttg gcattgccct     480
gagcacccac gccaacggtc tggactcgcc gcctatgttc gcaggtgcgg ggctgggagg     540
caacccgtgc cgcaagagct acgaggactg tactagtggt atcatggagg actccgccat     600
caaatgcgag tacatgctta acgccatccc caagcgcctg tgcctcgtgt gcggggacat     660
tgcctctggc taccactacg gagtggcctc ctgcgaggct tgcaaggcgt tcttcaagag     720
aaccattcaa ggcaacatcg agtacaactg cccggccacc aatgaatgtg agatcaccaa     780
acggaggcgc aagtcctgtc aggcctgccg attcatgaaa tgcctcaaag tggggatgct     840
gaaggaaggt gtgcgccttg accgagttcg aggaggccgc cagaagtaca agcgacggct     900
ggattcggag aacagcccct acctgaacct gccgatttcc ccacctgcta aaagccatt      960 gactaagatc gtctcgaatc tactagggt tgagcaggac aagctgtatg ctatgcctcc    1020
caacgatatc cccgagggag atatcaaggc cctgaccact ctctgtgaat tggcagatcg    1080
ggagcttgtg ttcctcatca actgggccaa gcacatccca gcttccca gtctgacact     1140 tgggaccag atgagcctgc tgcagagtgc ctggatggag attctcatct tgggcatcgt    1200
gtaccgctcg ctcccatacg atgacaagct ggcatacgcc gaggactata tcatggatga    1260
ggaacactct cgcctggtag ggctgctgga ccttaccga gccatcctgc agctggtgcg    1320
caggtacaag aaaactcaagg tagagaagga agagtttatg atcctcaagg ccctggccct    1380
cgccaactca gattcgatgt acattgagaa cctggaggcg gtgcagaagc tccaggacct    1440
gctgcacgag gcgctgcagg actatgagct gagtcagcgc cacgaggagc gcggagggc    1500
```

```
cggcaagctg ctgctgacgc tgcccctgct gaggcagaca gccgccaaag ccgtgcaaca    1560
cttctacagt gtgaaactgc agggcaaggt gcccatgcac aaactcttcc tggagatgct    1620
ggaggccaag gtgtgatggc ccagcacatg gacggacgga cacgatccaa gtggagacct    1680
ccacagccac cagcctcgac ttttttcaca cccgcatcgg ggctctgagc tgtcccagaa    1740 gaagggtct tcttgcttcc tggccatgtg cagactcctg ggacagcag atggggaggt     1800 ggggatgggg agggtagggg cgggggctc atctgtcacc cgcatttct ttggaatttt      1860 tttttccttt ctccatgggc agtgctaagg cttgggccag gacgacttc ccttagagct     1920 ggagaccacc agaggaagca gccttcctgc aagggatcca tttctggacc tctccctatt    1980
taggacctgg aggtatctgg atgggcagtg cttagtgccc gggacccaag agacatagat    2040
tgggggctcc tgaaggtgtt ggtgtcacgg tgggcagtcc cttggggcag aacgtctctg    2100
tggcctatcc cgaggctctg ttcctcctcc atctagctgg ctccctccac tttcccttt     2160 cttattgtcc cagtacaccc agttctcagt ggatgctcct gctagagtag ccacatcccc    2220
accccgaaga acccctcccc tgcttcctgc ccctacctca gccagccgga actcactggc    2280
tcagaaaaga gttgggttct gtacccactg ctcttttgc ctgctgtttc tccttctcct     2340
cttgggcatg ccagtctag aaacctatgg agaattcagg acctggcccc accagaggtc     2400
acttgaggga ctctcaaggt cagtagctta ggttggggtg taggatagca gagagaccca    2460
gcggtagagg gaaagtctca ttgcacctcg gaaaggaagg agctctaaag gtcccccttg    2520
gcccctccct tacctcataa aaaggcaagg cttggctttg tgccatagga gggcagcctc    2580
ctggcatttg caccagggat gtttgatgca gccctcctgg gtcaattccc ggcaagaccc    2640
tgcagtctgg ttgtcgtata gggtgctcca ccaacccacc gcagtcctaa aaccccctcag   2700 ccctaggcac atgaatgcac cttcaccca cccaaaaggc agtcccaggc tcatgctgtg     2760
tgtgtccttg ggtttgggtt gacaggatgt cctaaagatg aagcggttca ttctggaaaa    2820
tggacacgcc actttcatga caagtcctcc ggctttacct gctctgatcc cttcctggag    2880
tgcaagggtc ccctctttca ggcgttctgg cacctgccac tactgctggc tctgcctccc    2940
gggtgacacc tctaggagac tggtcacttc acagacttaa tgctaaactt ccccagagag    3000 ccttttccctg cccttttgcc cacaaagggg ttcatgcctc tgcatgggct ctccttgccc   3060
atgatccaag gtagatacca cttttgtgtt aaactgggtt aactcttagg ggctgggttt    3120
agctatcctg gcttctgaaa actcccccca gccacactgt ggagaggggg tgtcacctaa    3180
aattccacct agttctcaga atgtcttctg ggcctatgaa cacaccagca agggttggac    3240
aaacacccac agctgcctga gcggacacac tgctttgaag cagcagcagc agcagttaaa    3300
tgggcacctc ggctcggctc cttgatctag tgatgcaagc accccatacg gctgcttacc    3360
tgccgaagag aatggaccag tgacagttgg gtgccctgta gggaagctgg gtgccctggg    3420
cacctggagt cagagggtag agcccacttg ttcaaagact agccagatga gagacatctg    3480
tgatgccagg gtgctcaaaa caggaaaaag caagagagac cctctcctat tcccacctcc    3540
ccccagtcag agcaaaaacc caggctacct tccatatcca tttctggaac ccatggagag    3600
gaggcctctc tctgctagtg tgtattcaga taaagattat ttcaacccag aaatataaac    3660
atagctaacc ttgtaccttg tagaaggagg tgctggctgg gatctctttc tctcgttccc    3720 taaccttct gaagattctg gatggttctg gcgtgcctcc caggttttgc atccgtgaac     3780
agatgacttc ccatggacag agcttgagaa atacgaggct ctcatttggg cctagcaggg    3840
tcagagcctt tactatctgt gcctggtcct tccctccaga cttgactact catgagaaac    3900
```

| | |
|---|---|
| aggtggcagg caaggatgac agacgtgtga caaggagaca ggagggccca gagtccaagc | 3960 |
| ccatggaaca gcaccaaaga gaagcactat gtggagagat tgctttattt tctgataatg | 4020 |
| acgttgtggc tggaatgact taagatgtat atatttttta accggcagtc cttcgtgctg | 4080 |
| tctcacccc ctgtatggac atgtcctccc acggccctca tgtaaactac atgccctggg | 4140 |
| attatctccc atccagtccc atgtatctga atctaataa ataaggaaag gtctgctgaa | 4200 |
| aaaaaaaa | 4208 |

<210> SEQ ID NO 15
<211> LENGTH: 3029
<212> TYPE: DNA
<213> ORGANISM: Homo sapiens

<400> SEQUENCE: 15

| | |
|---|---|
| ccgcagagag gtgtggtcag ggacatttcc cctggccggg agcccatgga gcactgtcct | 60 |
| cagagatgcg caggttaggc tcactgtcta ggccaggccc accttagtca ctgtggactg | 120 |
| gcaatggaag ctcttcctgg acacacctgc cctagccctc accctggggt ggaagagaaa | 180 |
| tgagcttggc ttgcaactca gaccattcca cggaggcatc ctccccttcc tgggctggtg | 240 |
| aataaaagtt tcctgaggtc aaggacttcc ttttccctgc aaaatggtg tccagaactt | 300 |
| tgaggccaga ggtgatccag tgatttggga gctgcaggtc acacaggctg ctcagagggc | 360 |
| tgctgaacag gatgtcctcg gacgacaggc acctgggctc cagctgcggc tccttcatca | 420 |
| agactgagcc gtccagcccg tcctcgggca tcgatgccct cagccaccac agccccagtg | 480 |
| gctcgtccga cgccagcggc ggctttggcc tggccctggg cacccacgcc aacggtctgg | 540 |
| actcgccacc catgtttgca ggcgccgggc tgggaggcac cccatgccgc aagagctacg | 600 |
| aggactgtgc cagcggcatc atggaggact cggccatcaa gtgcgagtac atgctcaacg | 660 |
| ccatccccaa gcgcctgtgc ctcgtgtgcg gggacattgc ctctggctac cactacggcg | 720 |
| tggcctcctg cgaggcttgc aaggccttct tcaagaggac tatccaaggg aacattgagt | 780 |
| acagctgccc ggccaccaac gagtgcgaga tcaccaaacg gaggcgcaag tcctgccagg | 840 |
| cctgccgctt catgaaatgc ctcaaagtgg ggatgctgaa ggaaggtgtg cgccttgatc | 900 |
| gagtgcgtgg aggccgtcag aaatacaagc gacggctgga ctcagagagc agcccatacc | 960 |
| tgagcttaca aatttctcca cctgctaaaa agccattgac caagattgtc tcatacctac | 1020 |
| tggtggctga gccggacaag ctctatgcca tgcctccccc tggtatgcct gaggggggaca | 1080 |
| tcaaggccct gaccactctc tgtgacctgg cagaccgaga gcttgtggtc atcattggct | 1140 |
| gggccaagca catcccaggc ttctcaagcc tctccctggg ggaccagatg agcctgctgc | 1200 |
| agagtgcctg gatggaaatc ctcatcctgg gcatcgtgta ccgctcgctg cctatgacg | 1260 |
| acaagctggt gtacgctgag gactacatca tggatgagga gcactcccgc ctcgcggggc | 1320 |
| tgctggagct ctaccgggcc atcctgcagc tggtacgcag gtacaagaag ctcaaggtgg | 1380 |
| agaaggagga gtttgtgacg ctcaaggccc tggccctcgc caactccgat tccatgtaca | 1440 |
| tcgaggatct agaggctgtc cagaagctgc aggacctgct gcacgaggca ctgcaggact | 1500 |
| acgagctgag ccagcgccat gaggagccct ggaggacggg caagctgctg ctgacactgc | 1560 |
| cgctgctgcg gcagacggcc gccaaggccg tgcagcactt ctatagcgtc aaactgcagg | 1620 |
| gcaaagtgcc catgcacaaa ctcttcctgg agatgctgga ggccaaggtt ggccaagagc | 1680 |
| agcttagagg atctcccaag gatgaaagaa tgtcaagcca tgatgaaaa tgccccttcc | 1740 |

| | |
|---|---|
| aatcagctgc cttcacaagc agggatcaga gcaactcccc ggggatcccc aatccacgcc | 1800 |
| cttctagtcc aaccccccctc aatgagagag gcaggcagat ctcacccagc actaggacac | 1860 |
| caggaggcca gggaaagcat ctctggctca ccatgtaaca tctggcttgg agcaagtggg | 1920 |
| tgttctgcac accaggcagc tgcacctcac tggatctagt gttgctgcga gtgacctcac | 1980 |
| ttcagagccc ctctagcaga gtggggcgga agtcctgatg gttggtgtcc atgaggtgga | 2040 |
| agctgctttt atacttaaaa ctcagatcac aacaggaaat gtgtcagtaa caatggaact | 2100 |
| ccatccaatg ggaaagttcc tggtactgaa ggggtccatt ggacactcag aaaagaagtt | 2160 |
| caggggccaa cttcttagct ggaatcctgg ccagatgagg accctctccg ggaagggag | 2220 |
| aggactgact tagtggaagg tggtgaagtg aggagagttt aggggaacct tcccccagtg | 2280 |
| gaacagatct caagtttacc ctaaacctgc catttctgga aaatctgtaa agaggaaaca | 2340 |
| gcctgtctca gctgtactct catgatacag gtcatttgaa atgaaccaag aaataaaaca | 2400 |
| tgaaaatcca accatggaga aggtggtatg gctgggtttt gtttggtccc cttgtccta | 2460 |
| tacgttctaa agtttccaga ctggctttgt cactttgtga actcgtcatg tgtgaaaacc | 2520 |
| aatctttgca tatagggaac ttcctcgggc cacactttaa gaaccaagta agaggctctc | 2580 |
| aagactccag cagagtcggg aggccatggc agcgccttag aggagctgga acctgcaccc | 2640 |
| acctgtgtcg gtgggggggg cctcctttcc ccatagactc tgccctccct ctgtgcagat | 2700 |
| ggaagtggca ggggagggtg accagcttgt gacaagaaga ctgaagggtc cagagtccat | 2760 |
| gctcacggaa cagcaccaaa gaaaagcact atgtggaaag attgttttat tttctaataa | 2820 |
| tgataatatg gctggaatgg cttcttaaga tgtatatatt tttttaaaatg gcagttcccc | 2880 |
| attgcagcat cacctacttg tatgtctttc tgcctctgta tatgttctcc cagaaacccc | 2940 |
| catgtaaatc aaatgcccta ggatgcttcc atcctggtcc catgtatctg gaatctaata | 3000 |
| aataaggaaa ggaaaaaaaa aaaaaaaa | 3029 |

<210> SEQ ID NO 16
<211> LENGTH: 5312
<212> TYPE: DNA
<213> ORGANISM: Mus musculus

<400> SEQUENCE: 16

| | |
|---|---|
| ccaatcgggg ctttaagtcc ttgattagga gagagtgtgc gagcctcggt cccaactggc | 60 |
| cgtgcctatg ggcctgtcac caggagaacg cgtgtgttaa ttgcaccggg ctctgtcaag | 120 |
| gaaactttga tttataggtg gggtgcacaa ataatggttg tcgggcgcac atggattcgg | 180 |
| tagaactttg cctgcctgaa tcttttttccc tgcactacga agaagagctt ctctgcagaa | 240 |
| tgtcaaacaa agatcgacac attgattcca gctgttcgtc cttcatcaag acggaacct | 300 |
| ccagcccagc ctccctgacg gacagcgtca accaccacag ccctggtggg tcttccgacg | 360 |
| ccagtgggag ttacagttca accatgaatg gccatcagaa cggactggac tcgccaccctc | 420 |
| tctaccccctc tgctccgatc ctgggaggca gcgggcctgt ccggaaactg tatgatgact | 480 |
| gctccagcac catcgtagag gatccccaga ccaagtgtga atatatgctc aactccatgc | 540 |
| ccaagagact gtgcttagtg tgtggcgaca tcgcctctgg gtaccactat ggggttgcat | 600 |
| catgtgaagc ctgcaaggca ttcttcaaga ggacgattca aggtaacata gagtacagct | 660 |
| gcccagccac gaatgaatgt gagatcacaa agcgcagacg caaatcctgc caggcctgcc | 720 |
| gcttcatgaa gtgtctcaaa gtgggcatgc tgaaagaagg ggtccgtctt gacagagtgc | 780 |
| gtggaggtcg gcagaagtac aagcgcagaa tagatgctga gaacagccca tacctgaacc | 840 |

-continued

```
ctcagctggt gcagccagcc aaaaagccat ataacaagat tgtctcgcat ttgttggtgg      900
ctgaaccaga gaagatctat gccatgcctg accctactgt ccccgacagt gacatcaaag      960
ccctcaccac actctgtgac ttggctgacc gagagttggt ggttatcatt ggatgggcaa     1020
aacatattcc aggcttctcc acactgtccc tggcagacca atgagcctc ctccagagtg      1080 catggatgga gattctgatc ctcggcgttg tgtaccgatc gctttcgttt gaggatgaac     1140
ttgtctatgc agacgattat ataatggatg aagaccagtc taaattagca ggccttcttg     1200
acctaaataa tgctatcctg cagctggtga agaagtacaa gagcatgaag ctagagaagg     1260
aagaattcgt caccctcaaa gcaatagctc ttgctaattc agattccatg catatagaag     1320
atgtggaagc tgtgcagaaa cttcaggatg tgttacatga ggccctgcag gattacgagg     1380
ctggccagca catggaagac cctcgccgtg caggcaagat gctgatgacg ctgccgctgc     1440
tgaggcagac ctccaccaag gcagtccagc acttctacaa catcaaactc gaaggcaaag     1500
tgcccatgca caaacttttt ttggaaatgc tggaggccaa ggtctgacta aaagcccccc     1560
ctgggccctc ccatcctgca cgttgaaaag ggaagataaa cccaagaatg atgtcgaaga     1620
atcttagagt ttagtgaaca acattaaaaa tcaacagact gcactgatat tttagcagcc     1680
acagtacgat gcagcctgcg gattccgcta catcttcctg ataggtttcc tctactttat     1740
cccacgatcc tctggccaca tccctgcatt cctccactct tccttgttct attattatgt     1800
ttggcttctt tcactaatag ttcattttcc ctcctcccct cccttctctt ctccctccct     1860
cctctgtctc ccccttcctt cctttctctt cctttccaca atcttctcct cttgccttgc     1920
tctcacctct cttcgctttc tcacatctcc tcccactctg cgtacatagt caatacctct     1980
gattgtatgg aacatttctt ttacctcttg catctcttct ccgtctcttc cttccccact     2040
tttttttgtt tgtttgtttg tttcctttcc ttccttctgc tgctgaactc ttaatagcag     2100
tctctaactg gagagagaaa gagagagaga tggaagccag ccctgccaaa ggacagagat     2160
ccatactatg gatgccagtg aacttgtcat gaaccatgac atccccagtg agtaaggaat     2220
caaagagaga accgtaccta agtacattg caacgcaaac ggatcaactt agtgcagtat      2280
tagattctac cgggcagcct tcgatcagac aacctaagtg gcggcattgg ctgcttctcc     2340
ttgctttctc atctagatca gttacagcca tttgattcct taattctttt gtcaagtctt     2400
ccaggtgttg gttagtttag ctactatgta acttttttcag ggaatccttt aagctttatt    2460
cattcatgca atactagaga ggggtaagga taccgcaacc tcgtgctggc tttgaacaat     2520
tgaacactaa tgaaggacaa atgaaccctg aaggaagatt tttaaaaatg tttcgtttct     2580
tcttacaaat ggagattttt ttgtaccagc tttaccactt ttcagccatt tattaatatg     2640
gggatttaac ttactcaagc aatagttgaa gggaaggtgc atattaccac ggatgcaatt     2700
tatgttgtgt gccagtctgg tcccaaacat cagtttctta catgagctcc agtttgccta     2760
aatgttcact gacaccaagg attagatgat acctgccgtg acaccgagtg gtcccatcca     2820
cgagcactgc acatgggatc cctatctgta gaattagcac cagtacacct ccctgccggg     2880
agggacagtc gccataccggt ttctagctgc cctcgtggtt aggaacaaga tgctgcctgt    2940
atacaaactc tgtctcagaa ggagctgtga gccaatacca tttcagaggc aataaaggct     3000
aagtgccaga attcaaacca accaaccatc aaagacagca gacgcctgac caaattctaa     3060
agtcctgatc cataggagtc gattcactta ggaatggttg tttaaattaa cctgcaggtt     3120
tgttttgttt ccttgtttgt ttttttacca aaagctaagc caatagatgt gcttttttcaa    3180
```

| | |
|---|---|
| caagtatggt cacagcacga aggtcagtca ggtttcagac tgtaaccagg tgtaatctaa | 3240 |
| tgaagaaatc aaatgtcccc tcccgaaacc tacagtcgcc gaataaccag aaaccagtaa | 3300 |
| cctccgtaga acgctttacc aatggaccag tgttagtagc tgctctctgt attctgtgga | 3360 |
| cagtcttatt ctatgtacac agatgtaatt aaagttgtac tcctaacaaa caaaagaata | 3420 |
| gttcagcttc aatgttccat gtttgctgcg cttttctgaa ctttatgttg cattcagaaa | 3480 |
| ctgtcgtctt gttctcgtgg tgtttggatt cttgtggtgt gtgcttttag acacagggta | 3540 |
| gaattagaga cagtattgga tgtatacttc ctcaggagac tacagtagta tattctactc | 3600 |
| cttaccagta ataactaaga gattgaaact ccaaaacagt attcattacg atcagacaca | 3660 |
| catcaaaatc ataataatat tttcaaaaaa gggataattt ctctaatggt ttattataga | 3720 |
| ataccaatgt atagcttaga cataaaactt tgaatattca agaatataga taagtctaat | 3780 |
| ttttaaatgc tgtatataag gcttccacct gatcatctct cagatgttgt tattaactcg | 3840 |
| ctctgtgttg ttgcaaacct ttttggtgcg gacttgcttc caaaactatt gctactttgt | 3900 |
| gtgcgttaag caaaataccct tggactgagg gtgtctcagc cctgtgctag gaatactgtg | 3960 |
| tatctatcat tagctatatg gaatatatc gtagattgtg gttctcagta gagaaagtga | 4020 |
| ctgtagtgtg actctaggta aatcatcatt agcaattcat tcggatggtc aataacttga | 4080 |
| aattgatagc tgtgataagt tttaaaaaat tggcaaatcc ctgactaaac atcaacagaa | 4140 |
| aatacaactc ctgggggga aaggtgctca tcctgtaaga ttctttcatc atgtaagtgt | 4200 |
| ttgaaacatt actttgcaga aggtttatgc agggtttaag ttactaccgc tcaataatgc | 4260 |
| tatatataca caaatggaat atagacaatg tatgtaccca ccgtttcact gagtcgcaga | 4320 |
| gaagaatctg agcttcagaa gccagagccc acaagtgatc aggtgagaca gaggcacatt | 4380 |
| taaggaagga ggtacaatgt gtagttctcc gtttaaaaga cttggccttt taaaacaaca | 4440 |
| aatatctcac aactatggtg aaaacaacaa cagcttcaag tgtggatcta aaggaaacgc | 4500 |
| acaggtttag ggtaaatacc atttgtacct tgctcgagca aagtttattg tttttgttttt | 4560 |
| ttttgttttg ttttgttttg ttttcaagtt tccagcaaga ccgtttagtt aatgccagct | 4620 |
| gtcaggaaga taccaaggtg tatgttttag ccatgcaatt tgcagttta ttttccttttt | 4680 |
| aggtttgtcc ttatttaagg cagtgcgatt gttttggctt cttgtagtga ctctcgtgtt | 4740 |
| ttaatcaagc cagattgttg tatttattcc actattttgc atttaaatga tgacataaaa | 4800 |
| gatataaaaa atttaaaact gctatttttc ttatagaaga gaaaatggat gttggtgatt | 4860 |
| gtattttaat tatttaagca tctctgttta cctgcctggg acaacatttt atggcagtct | 4920 |
| tatgtgcaaa gatcgtgaat ggacaaaaca aaaaattaaa ctgcttacaa tgatccagga | 4980 |
| gttgcattat agccagtagt aaaaataata atgataatta ataataatta ataataataa | 5040 |
| tgaaaccatg tctatagctg taggtgggca tcacatctgt aaagcaatca attgtatatt | 5100 |
| tttgtgatgt gtaccatact gtgtgctcca gcaaatgtcc atttgtgtaa atgtatttat | 5160 |
| tttatattgt atatattgtt aaatgcaaaa aggagctatg attctgtgac tccaatcagt | 5220 |
| tcagatatgt aactcaaatt attatgcctt tcaggaggat ggtagaacaa tattaaacaa | 5280 |
| gcttccactt ttaaaaaaaa aaaaaaaaa aa | 5312 |

<210> SEQ ID NO 17
<211> LENGTH: 5260
<212> TYPE: DNA
<213> ORGANISM: Homo sapiens

<400> SEQUENCE: 17

```
aagctccaat cggggcttta agtccttgat taggagagtg tgagagcttt ggtcccaact    60
ggctgtgcct ataggcttgt cactaggaga acatttgtgt taattgcact gtgctctgtc   120
aaggaaactt tgatttatag ctggggtgca caaataatgg ttgccggtcg cacatggatt   180
cggtagaact ttgccttcct gaatcttttt ccctgcacta cgaggaagag cttctctgca   240
gaatgtcaaa caaagatcga cacattgatt ccagctgttc gtccttcatc aagacggaac   300
cttccagccc agcctccctg acggacagcg tcaaccacca cagccctggt ggctcttcag   360
acgccagtgg gagctacagt tcaaccatga atggccatca gaacggactt gactcgccac   420
ctctctaccc ttctgctcct atcctgggag gtagtgggcc tgtcaggaaa ctgtatgatg   480
actgctccag caccattgtt gaagatcccc agaccaagtg tgaatacatg ctcaactcga   540
tgcccaagag actgtgttta gtgtgtggtg acatcgcttc tgggtaccac tatgggggtag  600
catcatgtga agcctgcaag gcattcttca agaggacaat tcaaggcaat atagaataca   660
gctgccctgc cacgaatgaa tgtgaaatca caaagcgcag acgtaaatcc tgccaggctt   720
gccgcttcat gaagtgttta aaagtgggca tgctgaaaga aggggtgcgt cttgacagag   780
tacgtggagg tcggcagaag tacaagcgca ggatagatgc ggagaacagc ccatacctga   840
accctcagct ggttcagcca gccaaaaagc catataacaa gattgtctca catttgttgg   900
tggctgaacc ggagaagatc tatgccatgc ctgaccctac tgtccccgac agtgacatca   960
aagccctcac tacactgtgt gacttggccg accgagagtt ggtggttatc attggatggg  1020
cgaagcatat tccaggcttc tccacgctgt ccctggcgga ccagatgagc cttctgcaga  1080
gtgcttggat ggaaattttg atccttggtg tcgtataccg gtctctttcg tttgaggatg  1140
aacttgtcta tgcagacgat tatataatgg acgaagacca gtccaaatta gcaggccttc  1200
ttgatctaaa taatgctatc ctgcagctgg taaagaaata caagagcatg aagctggaaa  1260
aagaagaatt tgtcaccctc aaagctatag ctcttgctaa ttcagactcc atgcacatag  1320
aagatgttga agccgttcag aagcttcagg atgtcttaca tgaagcgctg caggattatg  1380
aagctggcca gcacatggaa gaccctcgtc gagctggcaa gatgctgatg acactgccac  1440
tcctgaggca gacctctacc aaggccgtgc agcatttcta caacatcaaa ctagaaggca  1500
aagtcccaat gcacaaactt tttttggaaa tgttggaggc caaggtctga ctaaaagctc  1560
cctgggcctt cccatccttc atgttgaaaa agggaaaata aacccaagag tgatgtcgaa  1620
gaaacttaga gtttagttaa caacatcaaa aatcaacaga ctgcactgat aatttagcag  1680
caagactatg aagcagcttt cagattcctc ataggttcc tgatgagttt ctttctactt    1740
tctccatcat cttctttcct ctttcttccc acatttctct ttctctttat tttttctcct  1800
tttcttcttt cacctccctt atttctttgc ttctttcatt cctagttccc attctccttt  1860
attttcttcc cgtctgcctg ccttcttttct tttctttacc tactctcatt cctctctttt  1920
ctcatccttc ccctttttc taaatttgaa atagctttag tttaaaaaaa aatcctccct  1980
tccccctttc ctttccctt ctttccttttt tccctttcct tttcccttttc ctttcctttc   2040
ctcttgacct tctttccatc tttcttttc ttccttctgc tgctgaactt ttaaaagagg    2100
tctctaactg aagagagatg gaagccagcc ctgccaaagg atggagatcc ataatatgga  2160
tgccagtgaa cttattgtga accatactgt ccccaatgac taaggaatca aagagagaga  2220
accaacgttc ctaaaagtac agtgcaacat atacaaattg actgagtgca gtattagatt  2280
tcatgggagc agcctctaat tagacaactt aagcaacgtt gcatcggctg cttcttatca  2340
```

```
ttgcttttcc atctagatca gttacagcca tttgattcct taattgtttt ttcaagtctt    2400
ccaggtattt gttagtttag ctactatgta acttttcag ggaatagttt aagctttatt    2460
cattcatgca atactaaaga gaaataagaa tactgcaatt ttgtgctggc tttgaacaat    2520
tacgaacaat aatgaaggac aaatgaatcc tgaaggaaga ttttaaaaa tgttttgttt    2580
cttcttacaa atggagattt ttttgtacca gctttaccac ttttcagcca tttattaata    2640
tgggaattta acttactcaa gcaatagttg aagggaaggt gcatattatc acggatgcaa    2700
tttatgttgt gtgccagtct ggtcccaaac atcaatttct taacatgagc tccagtttac    2760
ctaaatgttc actgacacaa aggatgagat tacacctaca gtgactctga gtagtcacat    2820
atataagcac tgcacatgag atatagatcc gtagaattgt caggagtgca cctctctact    2880
tgggaggtac aattgccata tgatttctag ctgccatggt ggttaggaat gtgatactgc    2940
ctgtttgcaa agtcacagac cttgcctcag aaggagctgt gagccagtat tcatttaaga    3000
ggcaataagg caaatgccag aattaaaaaa aaaatcatc aaagacagaa atgcctgac    3060
caaattctaa aacctaatcc ataaagttt attcatttag gaatgttcgt ttaaattaat    3120
ctgcagtttt taccaagagc taagccaata tatgtgcttt tcaaccagta ttgtcacagc    3180
atgaaagtca gtcaggttc cagactgtta agaggtgtaa tctaatgaag aaatcaatta    3240
gatgccccga atctacagt cgctgaataa ccaataaaca gtaacctcca tcaaatgcta    3300
taccaatgga ccagtgttag tagctgctcc ctgtattatg tgaacagtct tattctatgt    3360
acacagatgt aattaaaatt gtaatcctaa caaacaaaag aaatgtagtt cagcttttca    3420
atgtttcatg tttgctgtgc ttttctgaat tttatgttgc attcaaagac tgttgtcttg    3480
ttcttgtggt gtttggattc ttgtggtgtg tgcttttaga cacagggtag aattagagac    3540
aatattggat gtacaattcc tcaggagact acagtagtat attctattcc ttaccagtaa    3600
taaggttctt cctaataata attaagagat tgaaactcca acaagtatt cattatgaac    3660
agatacacat caaaatcata ataatatttt caaaacaagg aataatttct ctaatggttt    3720
attatagaat accaatgtat agcttagaaa taaaactttg aatatttcaa gaatatagat    3780
aagtctaatt tttaaatgct gtatatatgg ctttcactca atcatctctc agatgttgtt    3840
attaactcgc tctgtgttgt tgcaaaactt tttggtgcag attcgtttcc aaaactattg    3900
ctactttgtg tgctttaaac aaaataccct gggttgatga acatcaacc cagtgctagg    3960
aatactgtgt atctatcatt agctatatgg gactatattg tagattgtgg tttctcagta    4020
gagaagtgac tgtagtgtga ttctagataa atcatcatta gcaattcatt cagatggtca    4080
ataacttgaa atttatagct gtgataggag ttcagaaatt ggcacatccc tttaaaaata    4140
acaacagaaa atacaactcc tgggaaaaaa ggtgctgatt ctataagatt atttatatat    4200
gtaagtgttt aaaaagatta ttttccagaa agtttgtgca gggtttaagt tgctactatt    4260
caactcacact atatataaat aaaatatata caatatatac attgttttca ctgtatcaca    4320
ttaaagtact tgggcttcag aagtaagagc caaccaactg aaaacctgag atggagatat    4380
gttcaaagaa tgagatacaa ttttttagtt ttcagtttaa gtaactctca gcattacaaa    4440
agagtaagta tctcacaaat aggaaataaa actaaaacgt ggatttaaaa agaactgcac    4500
gggcttaggg gtaaatgctc atcttaaacc tcactagagg gaagtcttct caagtttcaa    4560
gcaagaccat ttacttaatg tgaagttttg gaaagttata aaggtgtatg ttttagccat    4620
atgattttaa ttttaatttt gcttctttta ggttcgttct tatttaaagc aatatgattg    4680
tgtgactcct tgtagttaca cttgtgtttc aatcagatca gattgttgta tttattccac    4740
```

```
tattttgcat ttaaatgata acataaaaga tataaaaaat ttaaaactgc tattttctt      4800 atagaagaga aaatgggtgt tggtgattgt attttaatta tttaagcgtc tctgtttacc     4860
tgcctaggaa aacattttat ggcagtctta tgtgcaaaga tcgtaaaagg acaaaaaatt     4920
taaactgctt ataataatcc aggagttgca ttatagccag tagtaaaaat aataataata    4980
ataataaaac catgtctata gctgtagatg ggcttcacat ctgtaaagca atcaattgta    5040 tattttgtg atgtgtacca tactgtgtgc tccagcaaat gtccatttgt gtaaatgtat     5100
ttattttata ttgtatatat tgttaaatgc aaaaaggaga tatgattctg taactccaat    5160
cagttcagat gtgtaactca aattattatg cctttcagga tgatggtaga gcaatattaa    5220
acaagcttcc acttttgact gctaaaaaaa aaaaaaaaa                            5260
```